(12) United States Patent
Schneider et al.

(10) Patent No.: US 10,263,168 B2
(45) Date of Patent: Apr. 16, 2019

(54) ATHLETIC ACTIVITY MONITORING DEVICE WITH ENERGY CAPTURE

(71) Applicant: NIKE, Inc., Beaverton, OR (US)

(72) Inventors: Summer Schneider, Portland, OR (US); Marcus Ward, Salem, OR (US); Jerry Wiant, Eugene, OR (US); Ingo Stark, Corvallis, OR (US)

(73) Assignee: NIKE, Inc., Beaverton, OR (US)

( * ) Notice: Subject to any disclaimer, the term of this patent is extended or adjusted under 35 U.S.C. 154(b) by 302 days.

(21) Appl. No.: 15/166,069

(22) Filed: May 26, 2016

(65) Prior Publication Data

US 2016/0346613 A1  Dec. 1, 2016

Related U.S. Application Data

(60) Provisional application No. 62/167,773, filed on May 28, 2015.

(51) Int. Cl.

| H01L 35/30 | (2006.01) |
|---|---|
| H01L 35/32 | (2006.01) |
| H01L 35/02 | (2006.01) |
| A43B 3/00 | (2006.01) |
| F03G 7/08 | (2006.01) |
| G06F 19/00 | (2018.01) |

(Continued)

(52) U.S. Cl.
CPC ............ *H01L 35/02* (2013.01); *A43B 3/0005* (2013.01); *A61B 5/681* (2013.01); *A61B 5/6807* (2013.01); *F03G 7/08* (2013.01); *G06F 19/3481* (2013.01); *G06Q 50/01* (2013.01); *H01L 35/30* (2013.01); *A61B 5/0024* (2013.01); *A61B 5/1123* (2013.01); *A61B 5/1128* (2013.01); *A61B 5/6804* (2013.01); *A61B 5/6895* (2013.01); *A61B 2505/09* (2013.01); *A61B 2560/0214* (2013.01); *A61B 2562/0219* (2013.01)

(58) Field of Classification Search
CPC .......... H01L 35/28; H01L 35/30; H01L 35/32
See application file for complete search history.

(56) References Cited

U.S. PATENT DOCUMENTS

| 4,183,156 A | * | 1/1980 | Rudy | ................... A43B 17/035 |
| | | | | 36/29 |
| 4,874,640 A | * | 10/1989 | Donzis | ................. A41D 31/005 |
| | | | | 36/37 |

(Continued)

FOREIGN PATENT DOCUMENTS

| EP | 2854190 A1 | 4/2015 |
| WO | 2008132109 A2 | 11/2008 |

OTHER PUBLICATIONS

Aug. 16, 2016—(WO) ISR & WO—App. No. PCT/US16/034410.

(Continued)

*Primary Examiner* — Edgardo San Martin
(74) *Attorney, Agent, or Firm* — Banner & Witcoff, Ltd.

(57) ABSTRACT

Aspects relate to an energy harvesting device adapted for use by an athlete while exercising. The device may utilize a mass of phase-change material to store heat energy, the stored heat energy subsequently converted into electrical energy by one or more thermoelectric generator modules. The energy harvesting device may be integrated into an item of clothing, and such that the mass of phase change material may store heat energy as the item of clothing is laundered.

7 Claims, 19 Drawing Sheets

(51) Int. Cl.
*G06Q 50/00* (2012.01)
*A61B 5/00* (2006.01)
*A61B 5/11* (2006.01)

(56) References Cited

U.S. PATENT DOCUMENTS

| | | | | |
|---|---|---|---|---|
| 4,906,502 | A | * | 3/1990 | Rudy ............... A43B 13/20 36/29 |
| 4,936,029 | A | * | 6/1990 | Rudy ............... A43B 13/203 36/153 |
| 5,042,176 | A | * | 8/1991 | Rudy ............... A43B 13/203 36/153 |
| 5,083,361 | A | * | 1/1992 | Rudy ............... A43B 13/189 156/145 |
| 5,235,715 | A | * | 8/1993 | Donzis ............. A41D 31/005 12/142 R |
| 5,722,482 | A | | 3/1998 | Buckley |
| 5,761,909 | A | * | 6/1998 | Hughes ............. A62B 9/003 165/DIG. 9 |
| 5,952,065 | A | * | 9/1999 | Mitchell ........... A43B 13/203 36/28 |
| 6,013,340 | A | * | 1/2000 | Bonk ............... A43B 1/0072 428/35.2 |
| 6,291,760 | B1 | * | 9/2001 | Mitamura .......... G04C 10/00 136/205 |
| 6,320,280 | B1 | * | 11/2001 | Kanesaka .......... G04C 10/00 307/72 |
| 6,560,167 | B1 | * | 5/2003 | Kotanagi .......... G04C 10/00 136/205 |
| 6,787,691 | B2 | * | 9/2004 | Fleurial ............ H01L 35/16 136/203 |
| 7,626,114 | B2 | * | 12/2009 | Stark ............... H01L 35/32 136/200 |
| 9,318,681 | B2 | * | 4/2016 | Gavillet ............ H01L 35/28 |
| 9,478,723 | B2 | * | 10/2016 | Fowler ............. H01L 35/30 |
| 9,748,463 | B2 | | 8/2017 | Schneider et al. |
| 9,748,464 | B2 | * | 8/2017 | Schneider ......... H01L 35/30 |
| 9,755,131 | B2 | | 9/2017 | Schneider et al. |
| 9,947,718 | B2 | * | 4/2018 | Schneider ......... H01L 27/16 |
| 9,947,852 | B2 | * | 4/2018 | Schneider ......... H01L 35/32 |
| 2002/0069906 | A1 | | 6/2002 | Macris |
| 2003/0041892 | A1 | * | 3/2003 | Fleurial ............ H01L 35/16 136/227 |
| 2004/0238022 | A1 | * | 12/2004 | Hiller .............. H01L 29/155 136/203 |
| 2008/0056429 | A1 | | 3/2008 | Tsubata |
| 2008/0135082 | A1 | | 6/2008 | Hirono et al. |
| 2008/0139894 | A1 | | 6/2008 | Szydlo-Moore et al. |
| 2008/0168775 | A1 | * | 7/2008 | Windheim .......... F25B 21/02 62/3.7 |
| 2008/0245068 | A1 | | 10/2008 | Bastawros et al. |
| 2008/0257395 | A1 | * | 10/2008 | Jovanovic .......... H01L 29/155 136/239 |
| 2009/0301539 | A1 | | 12/2009 | Watts |
| 2010/0006132 | A1 | * | 1/2010 | Hodes .............. H01L 35/30 136/224 |
| 2010/0187832 | A1 | | 7/2010 | Holland et al. |
| 2010/0212712 | A1 | | 8/2010 | Tran |
| 2012/0152297 | A1 | | 6/2012 | Mitchell et al. |
| 2012/0192910 | A1 | | 8/2012 | Fowler et al. |
| 2013/0087180 | A1 | | 4/2013 | Stark et al. |
| 2013/0098417 | A1 | | 4/2013 | Gavillet |
| 2013/0104425 | A1 | | 5/2013 | Kalra-Lall |
| 2013/0137957 | A1 | | 5/2013 | Wood et al. |
| 2013/0274587 | A1 | | 10/2013 | Coza et al. |
| 2013/0340801 | A1 | | 12/2013 | Zhang et al. |
| 2014/0288438 | A1 | | 9/2014 | Venkatraman et al. |
| 2014/0288876 | A1 | | 9/2014 | Donaldson |
| 2014/0299169 | A1 | | 10/2014 | Schneider et al. |
| 2014/0326287 | A1 | | 11/2014 | Wiant et al. |
| 2014/0358472 | A1 | | 12/2014 | Goel et al. |

OTHER PUBLICATIONS

Sep. 12, 2016—(WO) ISR & WO—App. No. PCT/US16/034363.
Snyder, "Small Thermoelectric Generators" The Electrochemical Society Interface, vol. 17, No. 3, pp. 54-56 (2008) See Figs. 1, 5.
Sep. 12, 2016—(WO) ISR & WO—App. No. PCT/US16/034358.
Aug. 29, 2016—(WO) ISR & WO—App. No. PCT/US16/034374.
Aug. 29, 2016—(WO) ISR & WO—App. No. PCT/US16/034381.
Sep. 5, 2016—(WO) ISR & WO—App. No. PCT/US16/034388.
Aug. 24, 2016—(WO) ISR & WO—App. No. PCT/US16/034398.
Aug. 24, 2016—(WO) ISR & WO—App. No. PCT/US16/034406.

* cited by examiner

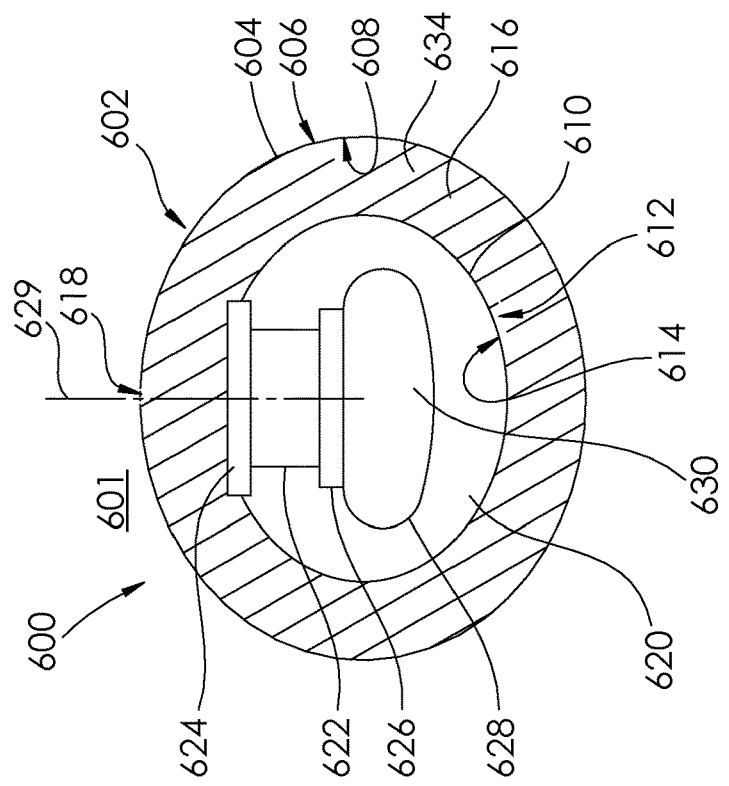
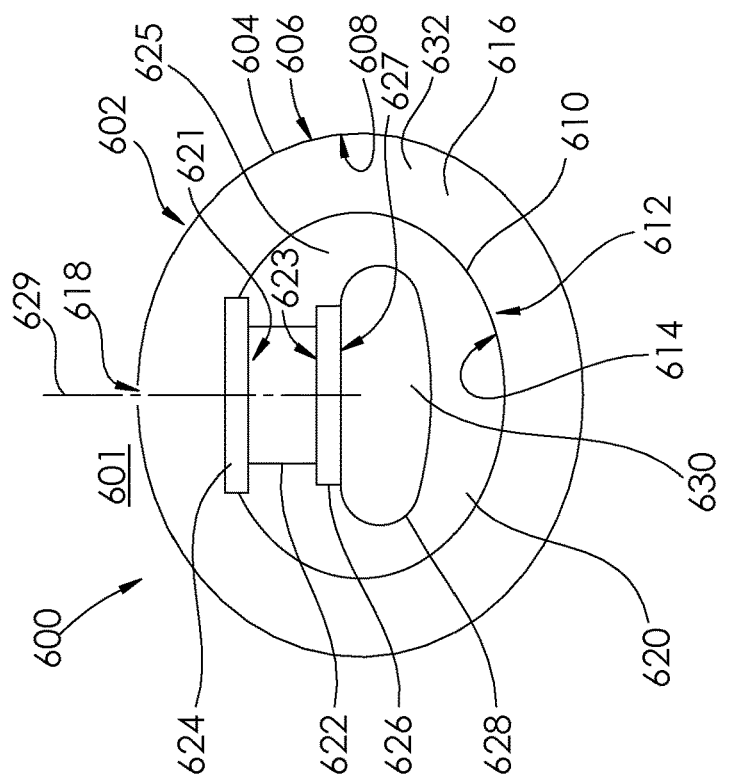

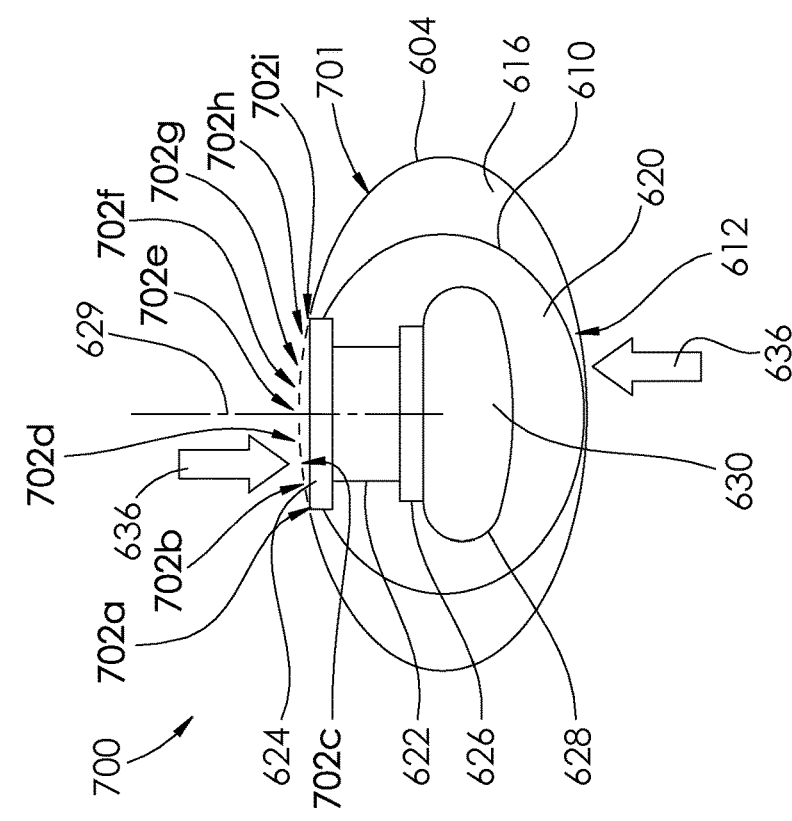
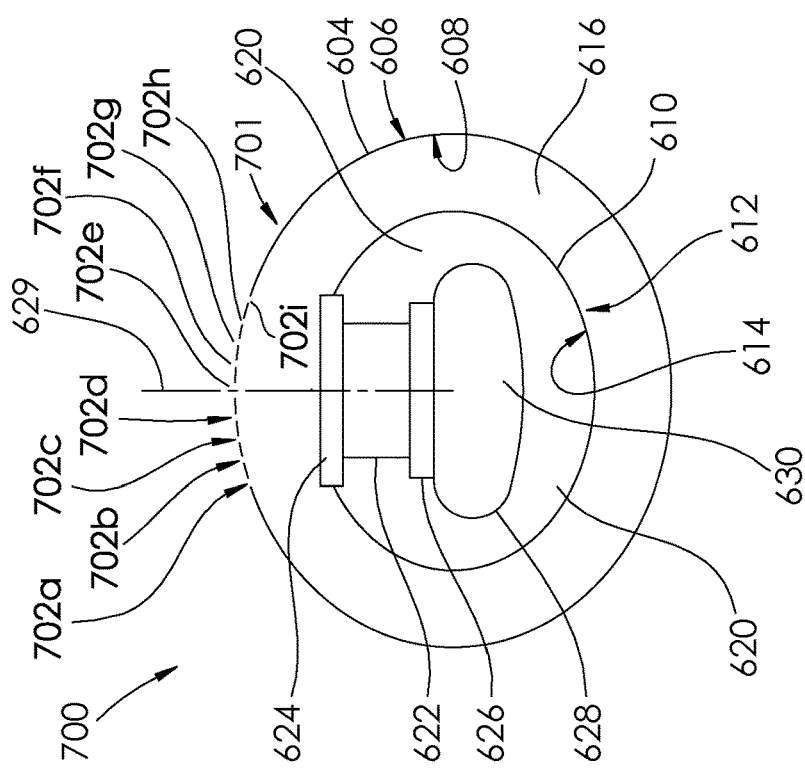

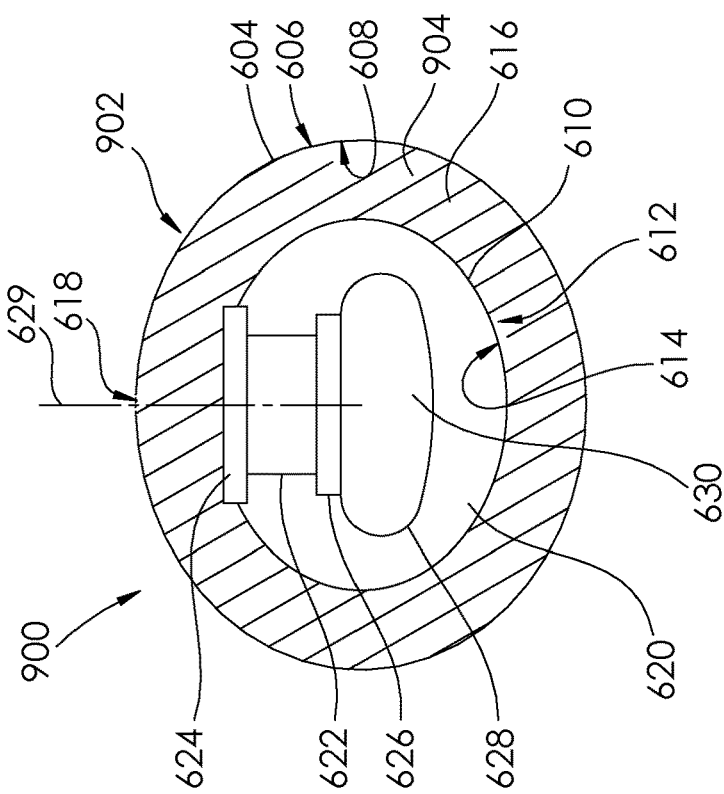
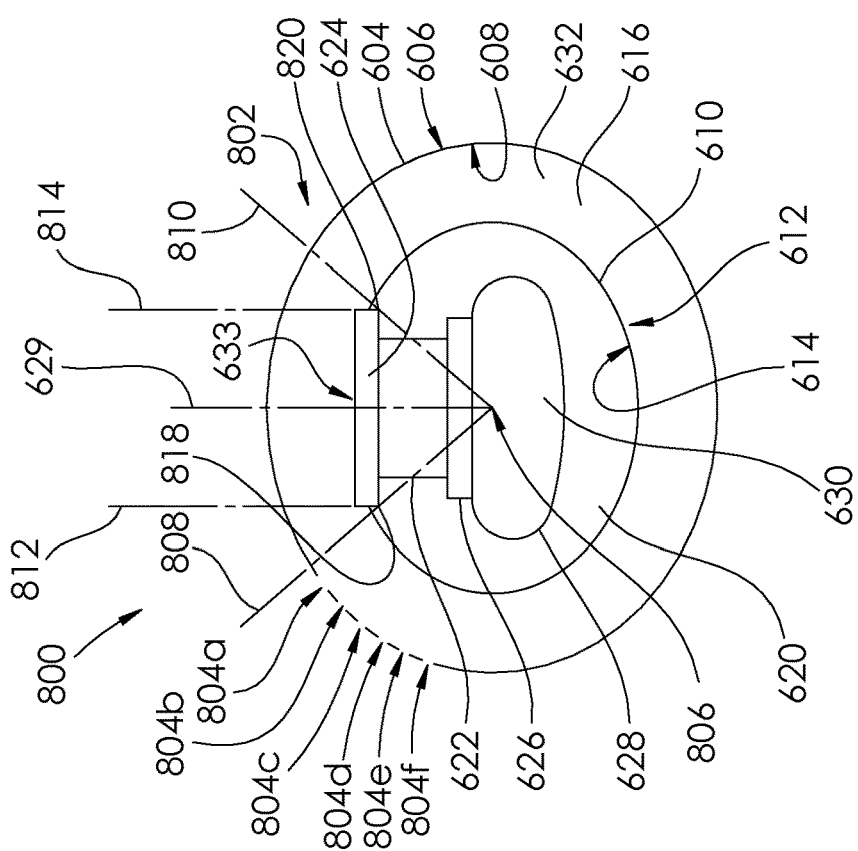
FIG. 9
FIG. 8

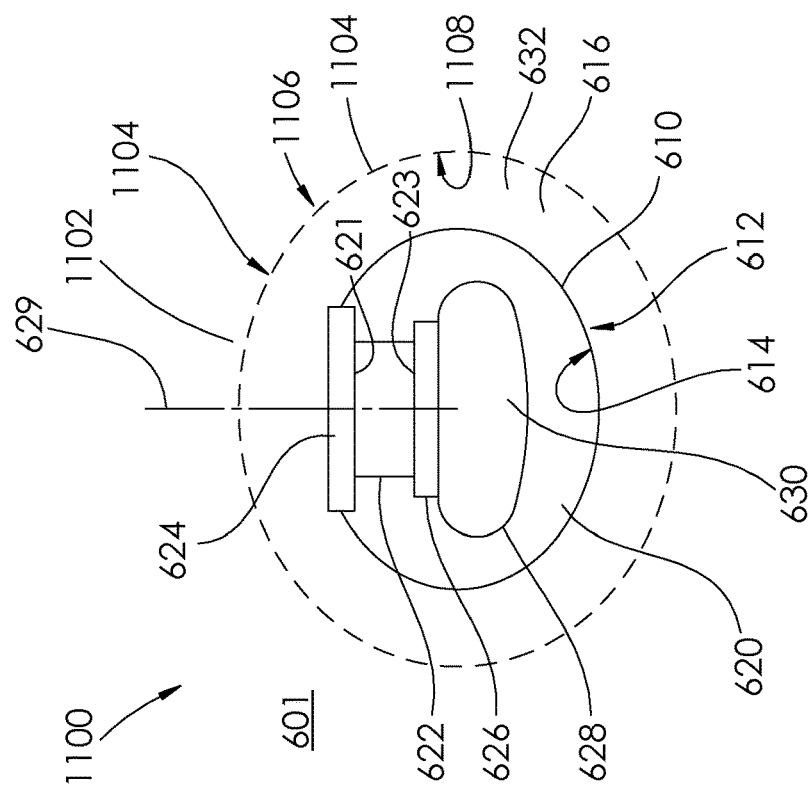
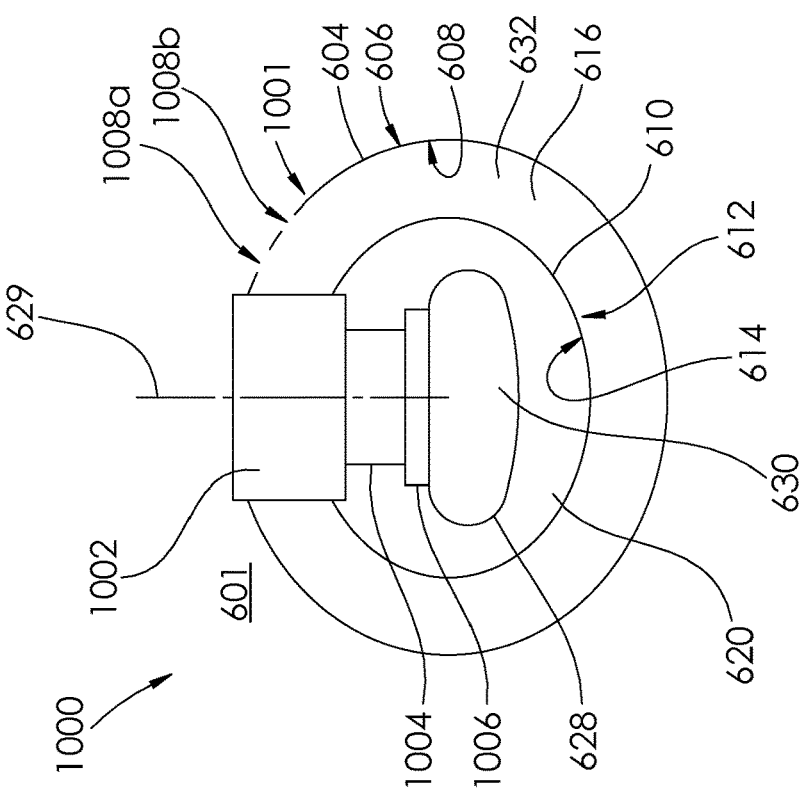
FIG. 11
FIG. 10

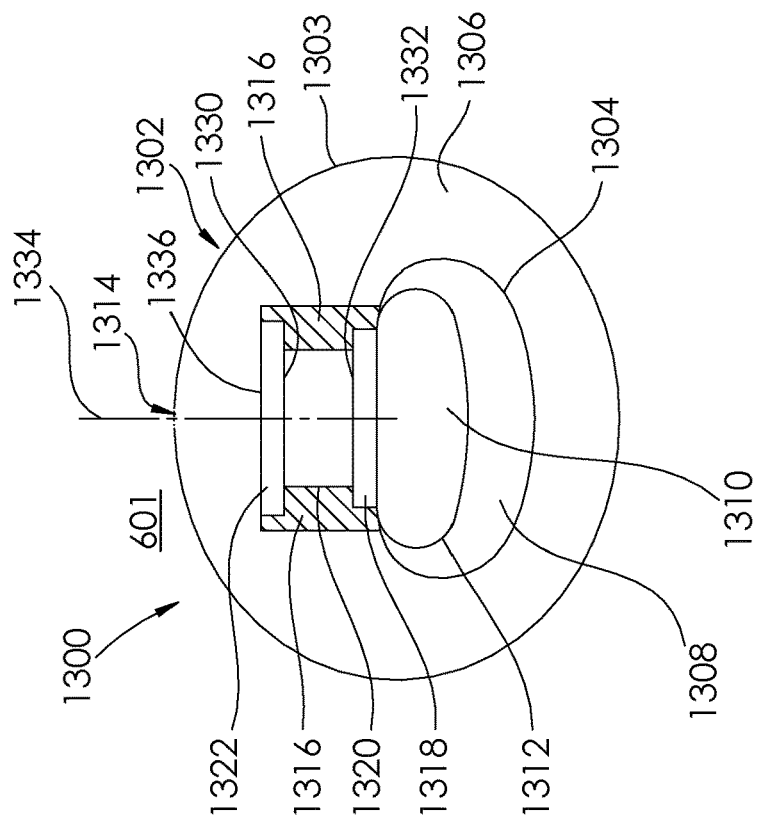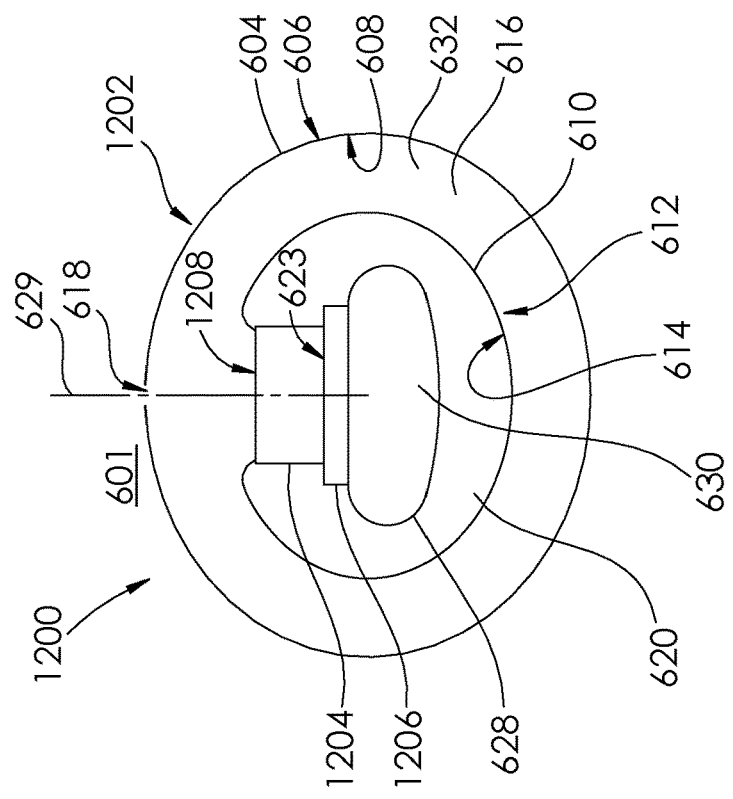

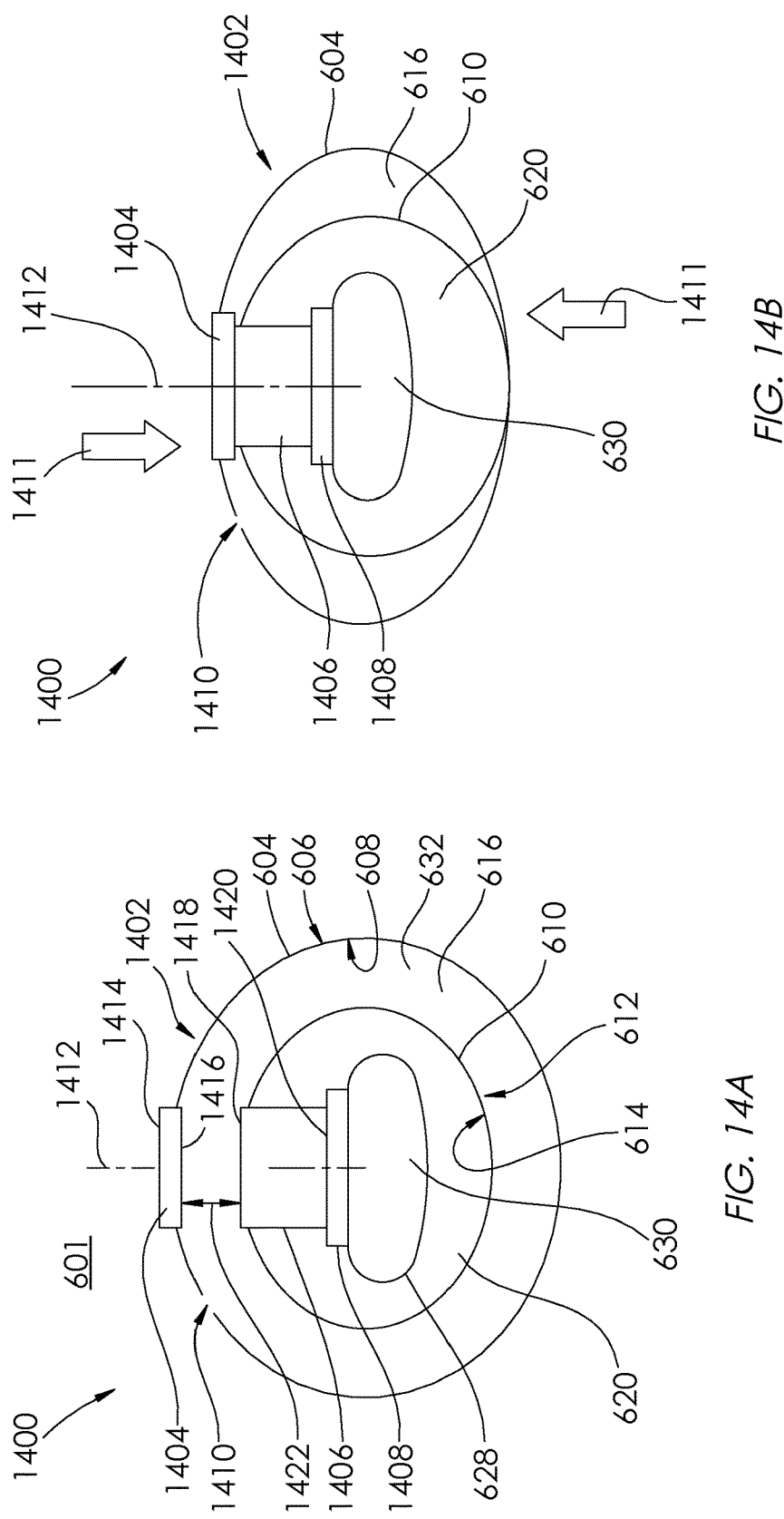

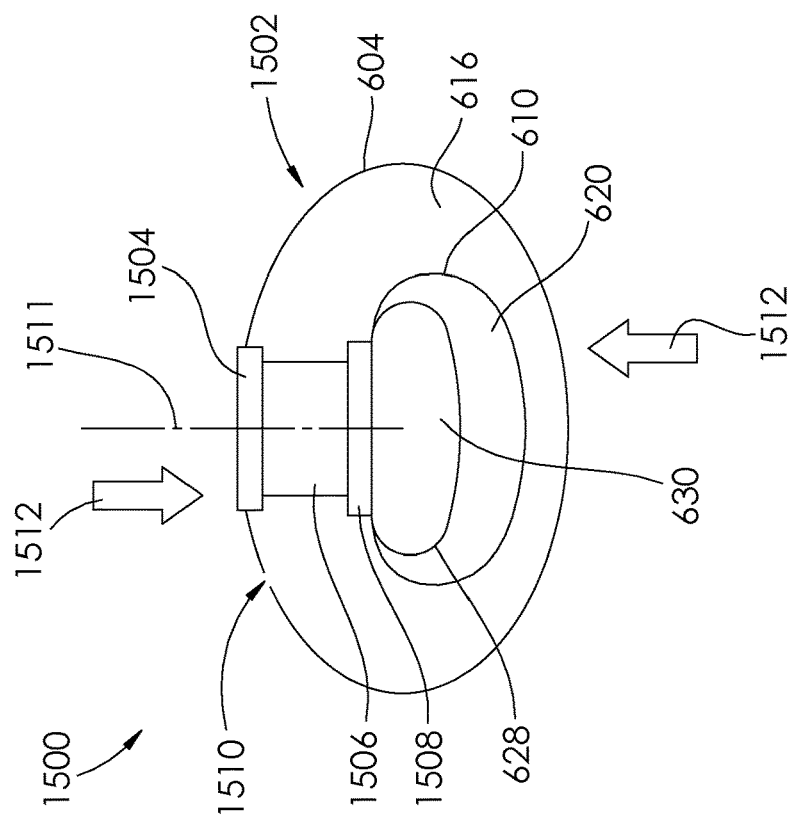
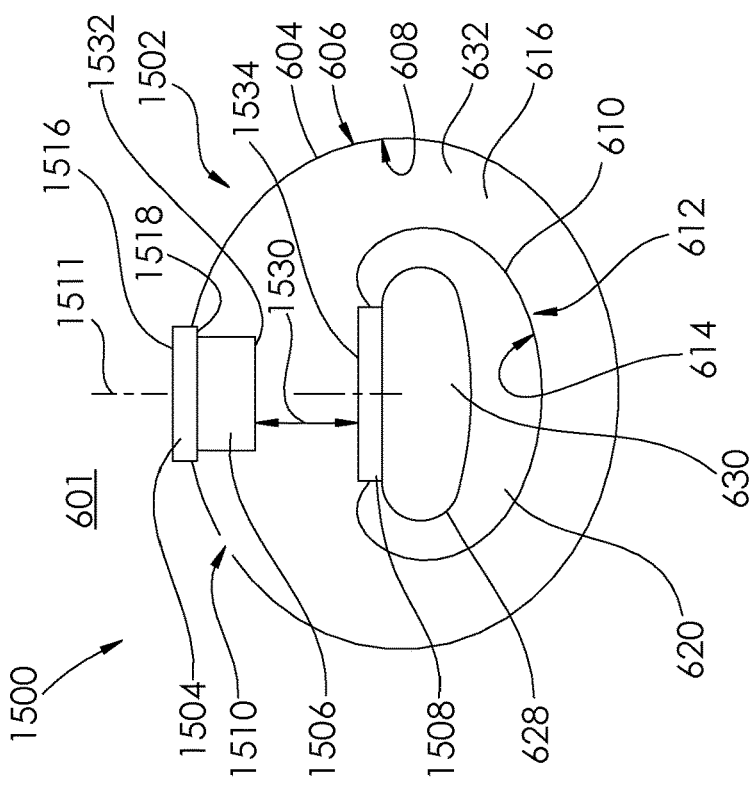
FIG. 15B
FIG. 15A

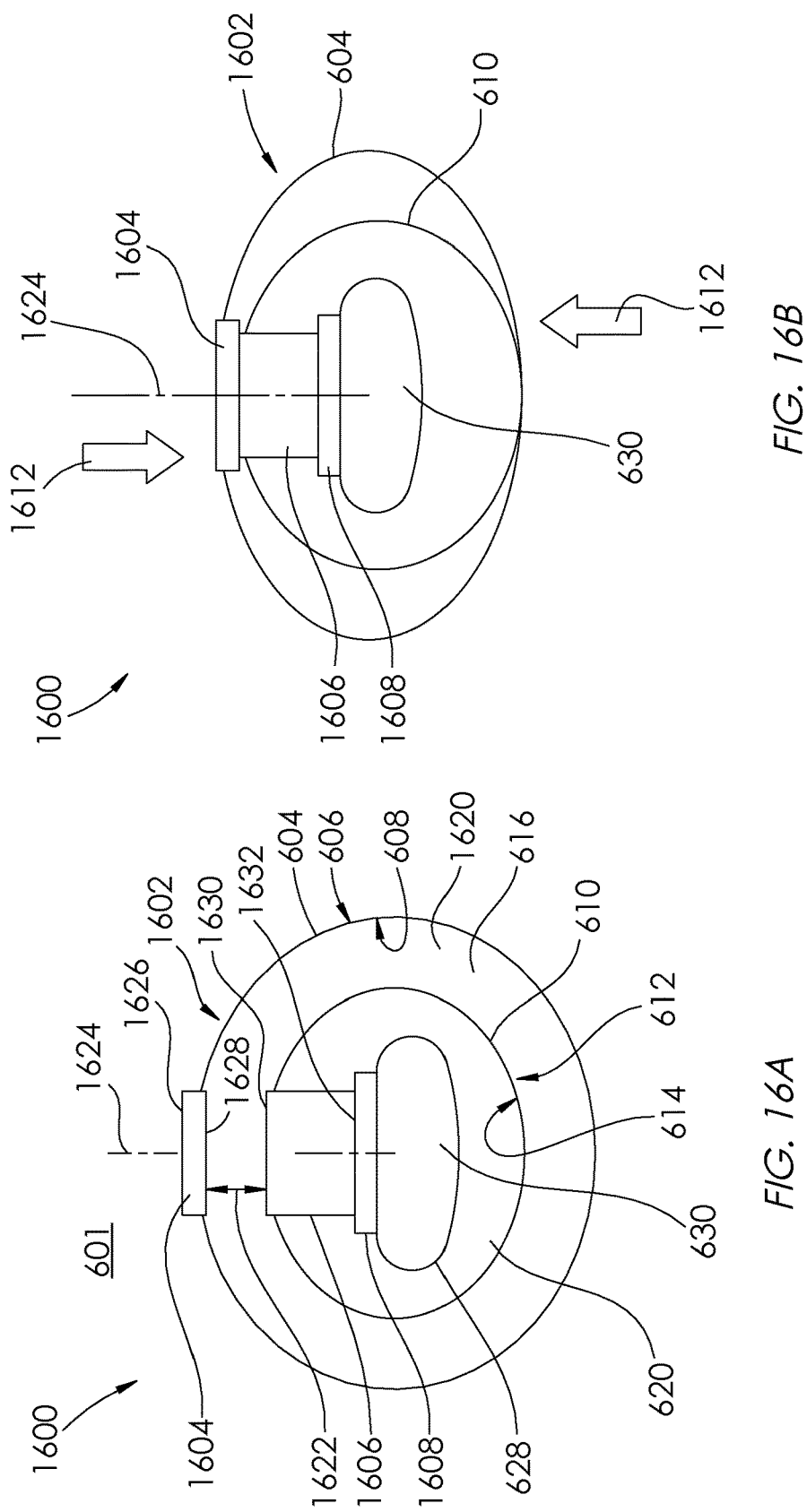

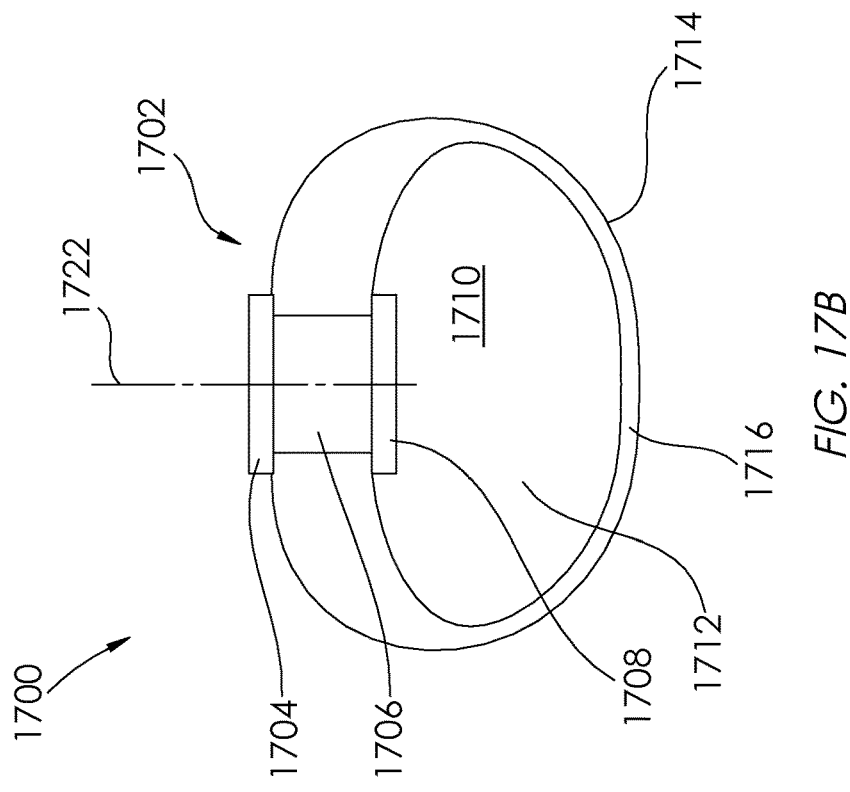
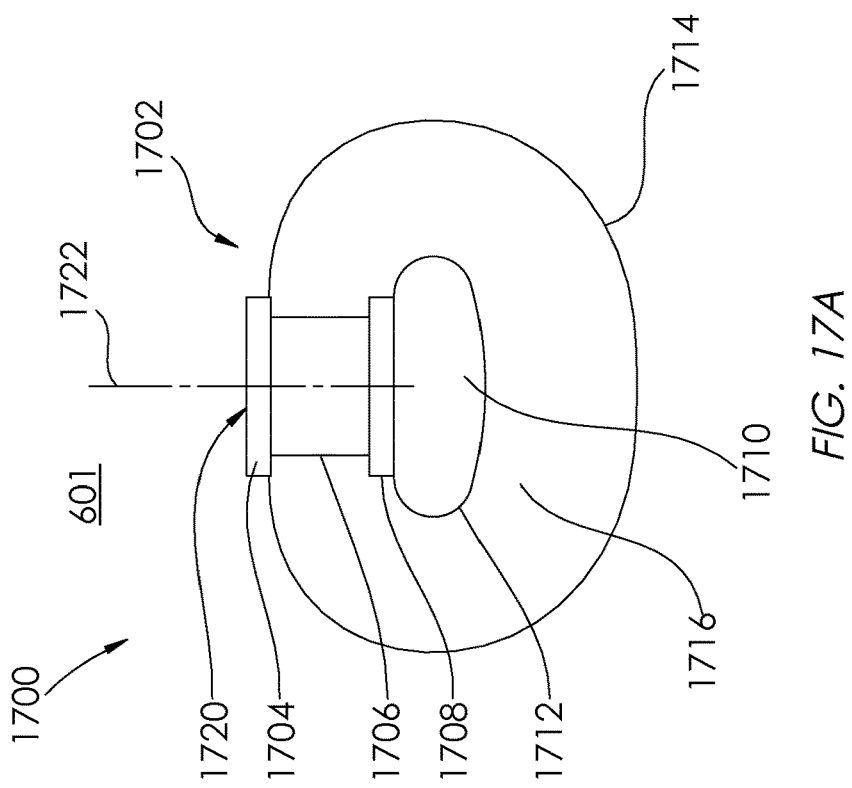
FIG. 17A
FIG. 17B

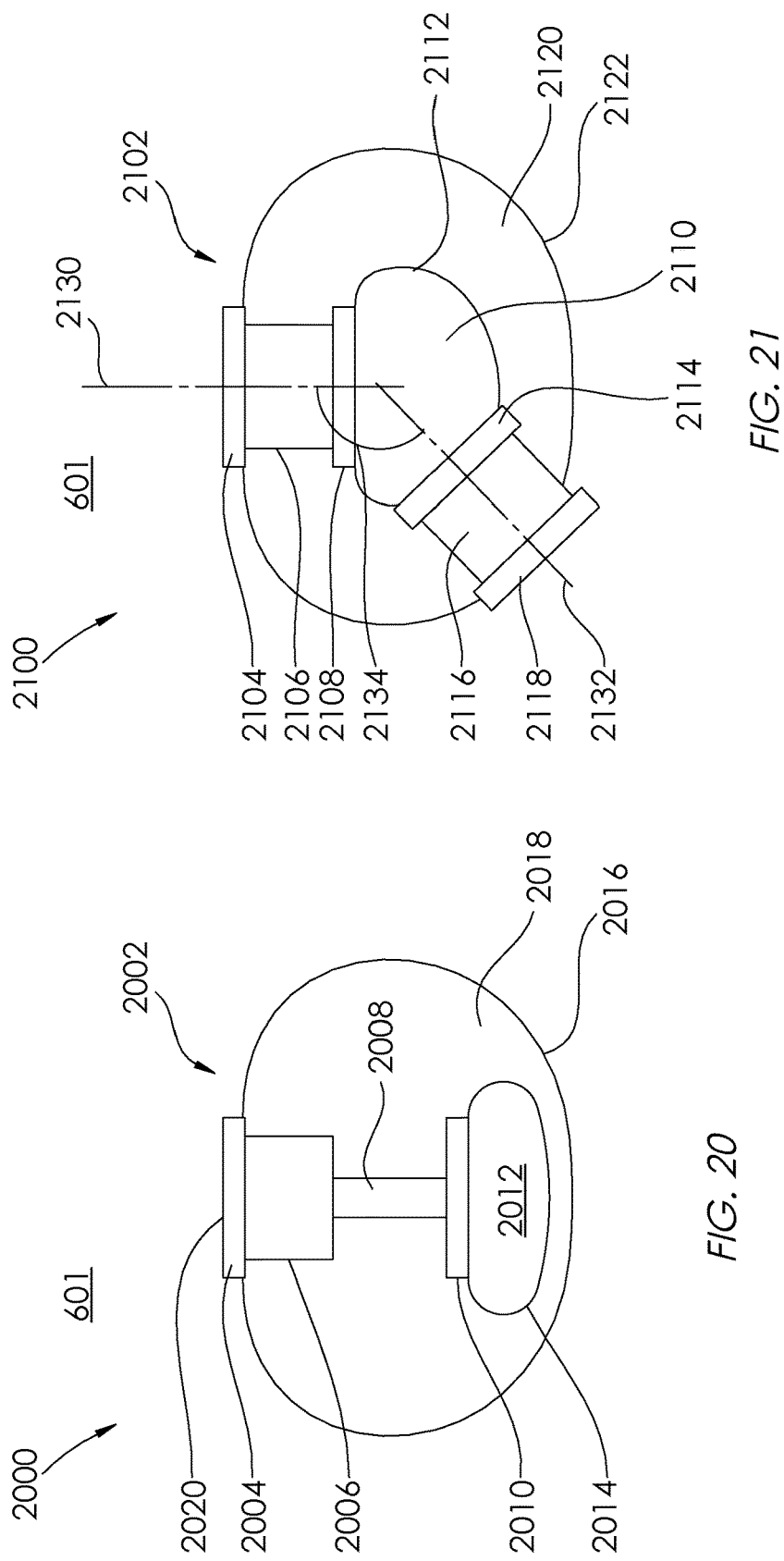

ATHLETIC ACTIVITY MONITORING DEVICE WITH ENERGY CAPTURE

CROSS-REFERENCE TO RELATED APPLICATIONS

This application claims priority to U.S. Provisional Patent Application No. 62/167,773, filed on May 28, 2015, which is expressly incorporated herein by reference in its entirety for any and all non-limiting purposes.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling. Devices for tracking a user's activity may offer motivation in this regard, providing feedback on past activity, and encouragement to continue with an exercise routine in order to meet various exercise goals.

However, existing tracking devices may require regular recharging of integrated battery elements. This need to plug an electronic tracking device into a wired power supply for recharging may be viewed as a chore, or may be overlooked at times, thereby reducing the consistency with which the activity tracking device is utilized by the user. In turn, this may reduce the efficacy with which the activity tracking device can provide motivation to the user to maintain a regular exercise program.

Therefore, improved systems and methods to address at least one or more of these shortcomings in the art are desired.

BRIEF SUMMARY

The following presents a simplified summary of the present disclosure in order to provide a basic understanding of some aspects of the invention. This summary is not an extensive overview of the invention. It is not intended to identify key or critical elements of the invention or to delineate the scope of the invention. The following summary merely presents some concepts of the invention in a simplified form as a prelude to the more detailed description provided below.

Aspects of the invention relate to a device for capturing, or harvesting, energy. This device may be adapted for positioning in or on an item of clothing. The energy harvesting device may have an insulated container with an outer membrane that has a first side in contact with an external environment, and a second side that defines the internal cavity. The insulated container may also have an outer heat exchanger that extends through the outer membrane, with at least one surface of the heat exchanger in contact with the external environment. Additionally, the insulated container may include a thermoelectric generator module within the internal cavity. As such, the thermoelectric generator may be sandwiched between the outer heat exchanger and an inner heat exchanger. The energy harvesting device may have a mass of phase-change material stored within the expandable membrane. A portion of the expandable membrane may be attached to the inner heat exchanger. The energy harvesting device may allow for bi-directional conduction of heat between the phase-change material and the external environment through the outer heat exchanger, the thermoelectric generator, and the inner heat exchanger. The phase-change material may be adapted to store a portion of heat energy absorbed from the external environment. This portion of heat energy may be captured from a dryer cycle as an item of clothing is laundered.

According to another aspect, an energy harvesting device may have a rigid container structure that has an outer membrane with an outer side in contact with the external environment, and an inner side defining an internal cavity. The energy harvesting device may also have a thermoelectric generator module. Heat may be conducted from the external environment through an outer heat exchanger to the thermoelectric generator module, and through to an inner heat exchanger. The inner heat exchanger may be in contact with a phase-change material. The outer heat exchanger, the thermoelectric generator, and the inner heat exchanger may facilitate bi-directional conduction of heat between the phase-change material and the external environment. The phase-change material may store a portion of heat energy absorbed from air in the external environment having a temperature in a range of approximately 45-85° C.

According to another aspect, an energy harvesting device may have a container structure that has an internal cavity and an outer membrane. The container structure may further include a thermoelectric generator module that is connected to an expandable membrane containing a mass of phase-change material. The thermoelectric generator may allow for bi-directional conduction of heat to and from the phase-change material. The phase-change material may store a portion of heat energy from an environment that has a temperature higher than a temperature of the phase-change material.

In another aspect, an energy harvesting device may be adapted for positioning within or on an item of clothing. The energy harvesting device may have an insulated container that has an outer membrane with an outer surface and an inner surface, the outer surface in contact with an external environment. The insulated container may also have an inner membrane, separated from the outer membrane, and having an outer surface and an inner surface. There may be an outer cavity positioned between the outer membrane and the inner membrane. The opening may extend from the outer surface of the outer membrane to the inner surface of the outer membrane. Air and/or water from the external environment may enter into the outer membrane through the opening. The energy harvesting device may additionally include an inner cavity defined by the inner membrane. An outer heat exchanger may extend through the inner membrane, with the inner membrane sealed around a portion of the outer heat exchanger. A thermoelectric generator may be located within the inner cavity, with the thermoelectric generator connected to the outer heat exchanger at a first side, and to an inner heat exchanger at a second side. A mass of phase-change material may be retained within the expandable membrane, with a portion of the expandable membrane connected to the inner heat exchanger. Bi-directional conduction of heat may be facilitated through the outer heat exchanger, the thermoelectric generator, and the inner heat exchanger, between the external environment and the phase-change material. The opening may allow water to enter into the outer cavity during a wash cycle as an item of clothing is laundered. The phase-change material may be adapted to store a portion of heat energy during a dryer cycle as the item of clothing is laundered.

In yet another aspect, an energy harvesting device may have an insulated container that has a permeable outer membrane with an outer surface and an inner surface. The insulated container may also have an inner membrane that is separated from the outer membrane, with the inner membrane having an outer surface and an inner surface. An outer cavity may be positioned between the outer membrane and inner membrane. An open-cell foam may at least partially filled the outer cavity. An inner cavity may be defined by the inner membrane. A thermoelectric generator may be positioned within the inner cavity. The thermoelectric generator may be connected to an outer heat exchanger at the first side, and an inner heat exchanger at a second side. The expandable membrane may enclose a mass of phase-change material, and at least a portion of the expandable membrane may be connected to the inner heat exchanger. The energy harvesting device may allow for bi-directional conduction of heat to and from the phase-change material. The permeable outer membrane may allow water to soak into the open-cell foam, and the phase-change material may store portion of heat energy captured from an external environment at a temperature ranging from approximately 45 to 85° C.

According to another aspect, an energy harvesting device may have an insulated container that has an outer membrane separated from an inner membrane. An outer cavity may be positioned between the outer membrane and the inner membrane. An inner cavity may be defined by the inner membrane. A thermoelectric generator module may be positioned within the inner cavity, and the thermoelectric generator may be attached to an expandable membrane that stores a mass of phase-change material. The outer membrane may be adapted to allow a liquid to enter into the outer cavity, and the phase-change material may be adapted to store portion of heat energy captured when the energy harvesting device is exposed to an external environment that has a temperature that is higher than the temperature of the phase change material.

According to one aspect, an energy harvesting device may be adapted for positioning within or on an item of clothing. The energy harvesting device may have an insulated container that has a deformable outer membrane in contact with an external environment. The insulated container may also have a deformable inner membrane that is separated from the outer membrane. An outer cavity may be positioned between the deformable outer membrane and the deformable inner membrane. An inner cavity may be defined by the deformable inner membrane. An outer heat exchanger may be attached to the deformable outer membrane, with the outer heat exchanger having an outer surface exposed to the external environment, and an inner surface exposed to the outer cavity. A thermoelectric generator may be positioned within the inner cavity, with the thermoelectric generator having an outer surface exposed to the outer cavity through the deformable inner membrane. The thermoelectric generator may also have an inner surface that is attached to an inner heat exchanger. The phase-change material membrane may be attached to the inner heat exchanger, and enclose a mass of phase-change material. The insulating container may be adapted to deform between an expanded configuration and a compressed configuration such that when in the expanded configuration, the inner surface of the outer heat exchanger is separated from the outer surface of the thermoelectric generator. In the compressed configuration, the inner surface of the outer heat exchanger may be adapted to contact the outer surface of the thermoelectric generator. The phase-change material may be adapted to store portion of thermal energy captured during a dryer cycle as the item of clothing is laundered.

According to another aspect, an energy harvesting device may have an insulated container that has a deformable outer membrane separated from a deformable inner membrane. The insulated container may have an outer cavity positioned between the default outer membrane and the deformable inner membrane. An inner cavity may be defined by the inner membrane. An outer heat exchanger may be connected to the deformable outer membrane, with the outer heat exchanger having an outer surface exposed to an external environment, and an inner surface exposed to the outer cavity. A thermoelectric generator may be positioned within the inner cavity, and have an outer surface exposed to the outer cavity through the deformable inner membrane. The thermoelectric generator may also have an inner surface attached to an inner heat exchanger. A phase-change material membrane may be attached to the inner heat exchanger, with the phase-change material membrane storing the mass of phase-change material. The insulated container may be deformed between an expanded configuration and a compressed configuration. When in the expanded configuration, the inner surface of the outer heat exchanger may be separated from the outer surface of the thermoelectric generator. When in the compressed configuration, the inner surface of the outer heat exchanger may be adapted to contact the outer surface of the thermoelectric generator. The phase-change material may be adapted to store portion of heat energy captured from air the external environment at a temperature ranging between approximately 45 and 85° C.

In yet another aspect, an energy harvesting device may have an insulated container that has an insulating material positioned between a deformable outer membrane and a deformable inner membrane. The deformable inner membrane may define an internal cavity. A thermoelectric generator may be positioned within the internal cavity, and have a first surface exposed to the insulating material through the deformable inner membrane. The thermoelectric generator may have a second surface that is attached to a phase-change material membrane that contains the mass of phase-change material. The insulated container may be configured to be deformed between an expanded configuration and a compressed configuration and the phase-change material may be configured to store portion of heat energy captured when the energy harvesting device is exposed to a high temperature environment.

According to one aspect, an energy harvesting device may be adapted to be integrated into an item of clothing. The energy harvesting device may have an insulated container adapted to be transitioned between an expanded configuration and a compressed configuration. The insulated container may also have a deformable outer membrane separated from the deformable inner membrane. An outer cavity may be positioned between the deformable outer membrane of the deformable inner membrane. An inner cavity may be defined by the deformable inner membrane. An outer heat exchanger may be attached to the deformable outer membrane, with the outer heat exchanger having an outer surface exposed to an external environment, and an inner surface exposed to the outer cavity. A thermoelectric generator may be positioned within the inner cavity, and have an outer surface exposed to the outer cavity through the deformable inner membrane, and an inner surface attached to an inner heat exchanger. An activity monitoring circuit may be connected to, and powered by, the thermoelectric generator such that an output of the thermoelectric generator is connected to an interrupt input of the activity monitoring circuit. A phase-change material membrane may be joined to the inner heat exchanger, and store a mass of phase change material. The primary axis of conduction through the inner heat exchanger, the thermoelectric generator, and the outer heat exchanger may have a first thermal conductivity in the insulated container is in the expanded configuration and a second thermal conductivity in the insulated containers in the compressed configuration. When transitioned from the expanded configuration to the compressed configuration, a voltage output from the thermoelectric generator at the interrupt input may transition the activity monitoring circuit from a first power configuration to a second power configuration.

In another aspect, an energy harvesting device may comprise an insulated container adapted to be transitioned between an expanded configuration and a compressed configuration. The insulated container may have a deformable outer membrane separated from a deformable inner membrane. The cavity may be positioned between the deformable outer membrane and the deformable inner membrane. The outer heat exchanger may be attached to the deformable outer membrane, and have an outer surface exposed to an external environment, and an inner surface exposed to the cavity. A thermoelectric generator may be positioned within the insulated container, and have an outer surface exposed to the cavity through the deformable inner membrane, and an inner surface attached to an inner heat exchanger. An activity monitoring circuit may be powered by the thermoelectric generator. The phase-change material membrane may be joined to the inner heat exchanger, and store a mass of phase-change material. The primary axis of conduction through the inner heat exchanger, the thermoelectric generator, and the outer heat exchanger may have a first thermal conductivity when the insulated container is in the expanded configuration, and a second thermal conductivity, greater than the first thermal conductivity, an insulating container is in the compressed configuration. The thermoelectric generator may output a first voltage when the insulated container is in the expanded configuration, and a second voltage, higher than the first voltage, when in the compressed configuration.

In yet another aspect, an energy harvesting device may have an insulated container adapted to be transitioned between an expanded configuration and a compressed configuration. The insulating container may have a cavity positioned between a deformable outer membrane and an inner membrane. An outer heat exchanger may be joined to the deformable outer membrane, and have an outer surface exposed to an external environment, and an inner surface exposed to the cavity. The energy harvesting device may further have a thermoelectric generator that has an outer surface exposed to the cavity through the inner membrane, and an inner surface joined to an inner heat exchanger. A phase-change material membrane may be joined to the inner heat exchanger, and store a mass of phase-change material. The primary axis of conduction through the inner heat exchanger, the thermoelectric generator, and the outer heat exchanger may have a first thermal conductivity when the insulated container is in the expanded configuration, and a second thermal conductivity, greater than the first thermal conductivity, when the insulated container is in the compressed configuration. The thermoelectric generator may output a first voltage when the insulated container is in the expanded configuration, and a second voltage, higher than the first voltage when in the compressed configuration.

According to another aspect, an activity monitoring device may have a support structure that has a first end separated from a second end along a first axis. The support structure may further have a first side exposed to an external environment, and a second side, opposite the first side, adapted to be positioned close to an area of skin of the user. The activity monitoring device may further have a processor, an activity monitoring circuit coupled to the support structure, and a non-transitory computer-readable medium configured to obtain sensor data from the activity monitoring circuit. Further, athletic measurements may be calculated based upon the sensor data. The activity monitoring device may further have at least two series-connected thermoelectric generator modules adapted to generate and transfer electrical energy to the processor and the activity monitoring circuit. As such, the thermoelectric generator modules may be adapted to generate electrical energy responsive to a thermal gradient between the first side and the second side.

In another aspect, an activity monitoring device may have a flexible support structure that has a first end separated from a second end. The device may further have a first coupling mechanism at the first end that is adapted to be removably-coupled to a second coupling mechanism at the second end. The support structure may further have a first side adapted to be exposed to an external environment, and a second side, opposite the first side, adapted to be positioned close to an area of skin of a user. The activity monitoring device may have an activity monitoring circuit joined to the flexible support structure, and at least two series-connected thermoelectric generator modules that are adapted to generate an transfer electrical energy to a processor and an activity monitoring circuit. The thermoelectric generator modules may be adapted to generate electrical energy in response to a thermal gradient between the first side and the second side. The activity monitoring device may further have non-transitory computer-readable media adapted to receive sensor data from the activity monitoring circuit, and determine that the sensory data is indicative of a threshold level of athletic movement. In response, the computer-readable media may be adapted to cause the activity monitoring device to enter into a first active state. Further, athletic measurements may be calculated based upon the user's athletic movements, and the activity monitoring device may be switched into a second active state.

In yet another aspect, an activity monitoring device may have a flexible support structure that has a multiple individual, rigid, interconnected components. The support structure may have a first side adapted to be exposed to an external environment, and a second side opposite the first side, adapted to be positioned close to an area of skin of a user. The activity monitoring device may also have an activity monitoring circuit joined to the flexible support structure, and at least two series-connected thermoelectric generator modules. The thermoelectric generator modules may be adapted to generate an transfer electrical energy to a processor and the activity monitoring circuit in response to a thermal gradient between the first side and the second side. The activity monitoring device may also have a non-transitory computer-readable medium may be adapted to obtain sensor data from the activity monitoring circuit, and calculated athletic measurements based upon the sensor data. Additionally, the activity monitoring device may have a transceiver adapted to automatically transmit the calculated athletic measurements to a mobile device.

BRIEF DESCRIPTION OF THE DRAWINGS

FIG. 6A schematically depicts an energy harvesting device in a first configuration having an outer cavity filled with a mass of air, according to one or more aspects described herein;

FIG. 6B schematically depicts an energy harvesting device having a mass of fluid within an outer cavity, which may, in certain embodiments, be a second configuration of the energy harvesting device of FIG. 6A, according to one or more aspects described herein;

FIG. 7A schematically depicts another implementation of an energy harvesting device in which it may be configured with an insulated container having an outer membrane with a plurality of apertures, according to one or more aspects described herein;

FIG. 7B schematically depicts an energy harvesting device in a compressed configuration, according to an example embodiment of the innovation;

FIG. 8 schematically depicts another implementation of an energy harvesting device in which an insulated container includes an outer membrane 604 with a plurality of apertures, according to one or more aspects described herein;

FIG. 9 schematically depicts another implementation of an energy harvesting device, according to one or more aspects described herein;

FIG. 10 depicts another implementation of an energy harvesting device, according to one or more aspects described herein;

FIG. 11 schematically depicts another implementation of an energy harvesting device, according to one or more aspects described herein;

FIG. 12 schematically depicts another implementation of an energy harvesting device, according to one or more aspects described herein;

FIG. 13 schematically depicts another implementation of an energy harvesting device, according to one or more aspects described herein;

FIGS. 14A and 14B schematically depict another implementation of an energy harvesting device, according to one or more aspects described herein, in which the device may be configured to deform, or compress, between an expanded configuration, as depicted in FIG. 14A, and a compressed configuration, as depicted in FIG. 14B;

FIGS. 15A and 15B schematically depict another implementation of an energy harvesting device, according to one or more aspects described herein, in which a thermoelectric generator is spaced apart from an inner heat exchanger when the energy harvesting device is in an expanded configuration, and positioned proximate the inner heat exchanger when the energy harvesting device is in a compressed configuration;

FIGS. 16A and 16B schematically depict another implementation of an energy harvesting device, according to one or more aspects described herein, in which an outer heat exchanger is spaced apart from a thermoelectric generator when the energy harvesting device is in an expanded configuration, and positioned proximate the thermoelectric generator when the energy harvesting device is in a compressed configuration;

FIGS. 17A and 17B schematically depict another implementation of an energy harvesting device, according to one or more aspects described herein;

FIG. 20 schematically depicts another implementation of an energy harvesting device, according to one or more aspects described herein, in which the device may comprise an insulated container that has an outer membrane encapsulating an internal cavity;

FIG. 21 schematically depicts another implementation of an energy harvesting device, according to one or more aspects of the innovation that comprises multiple thermoelectric generators;

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
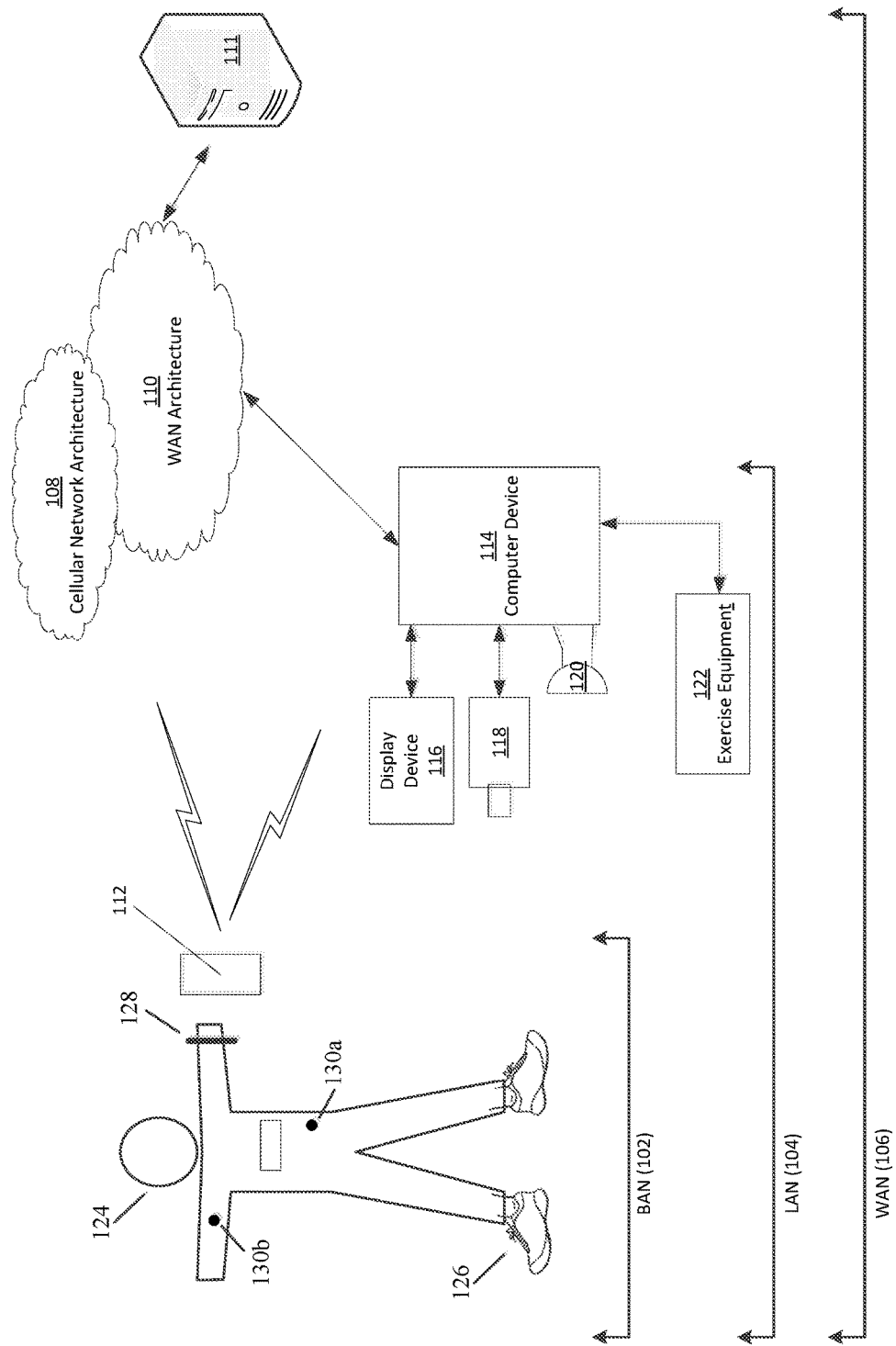
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
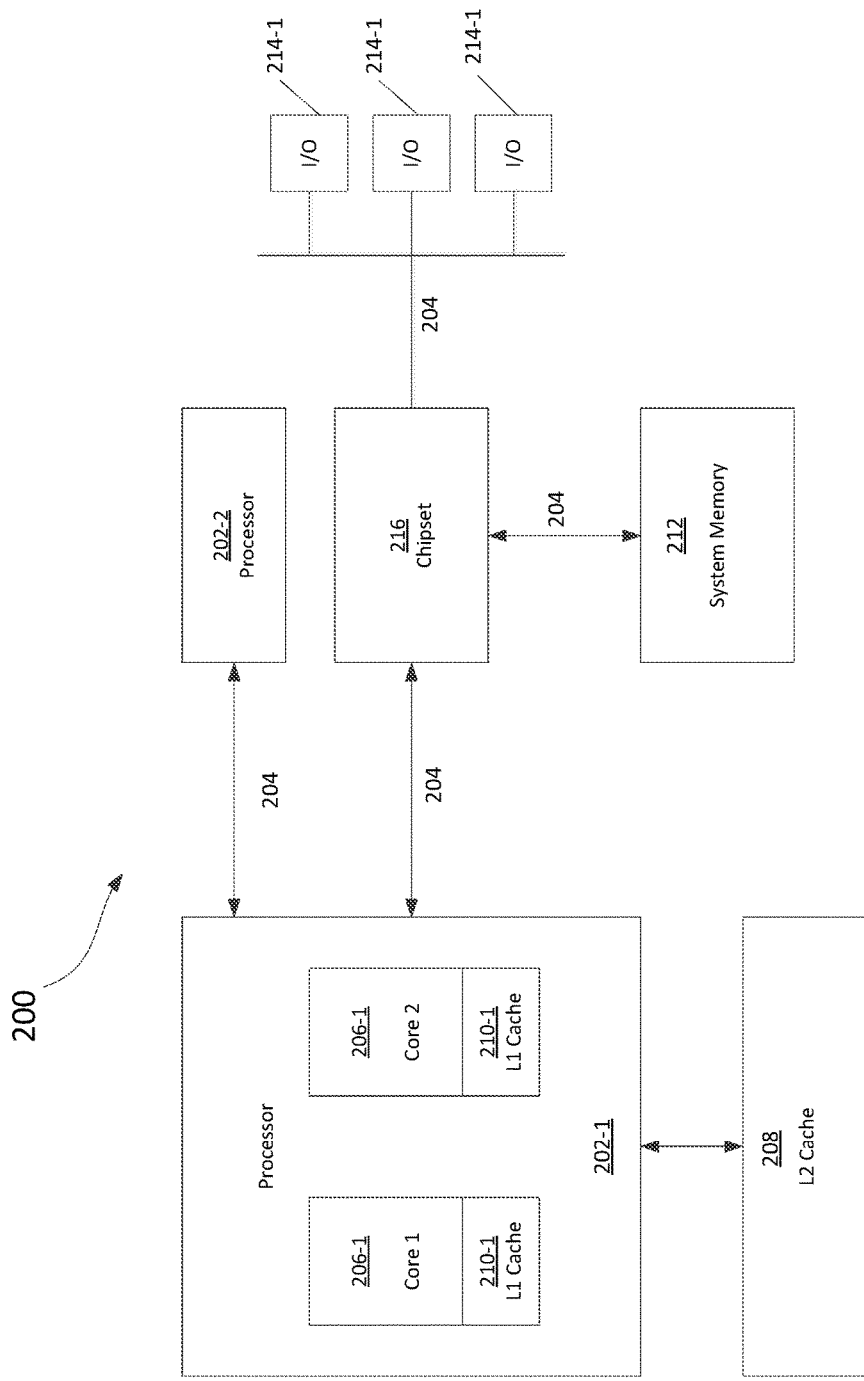
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
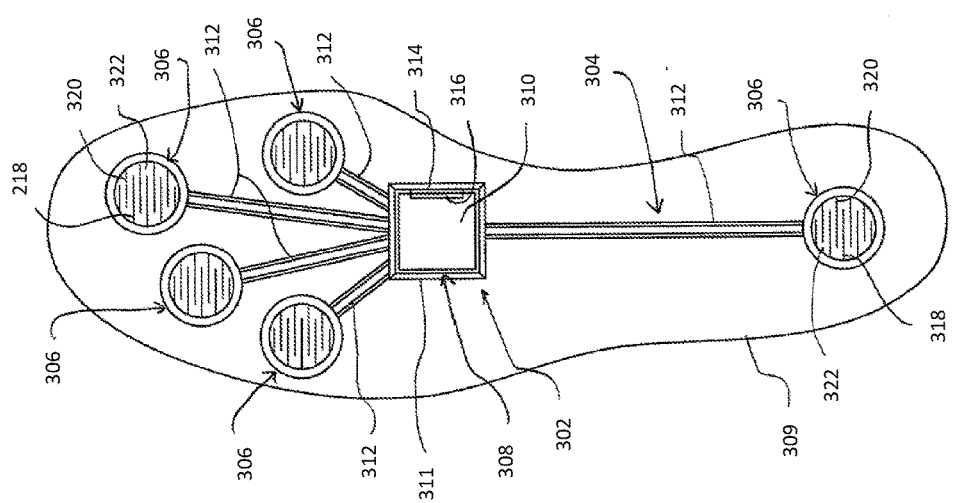
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
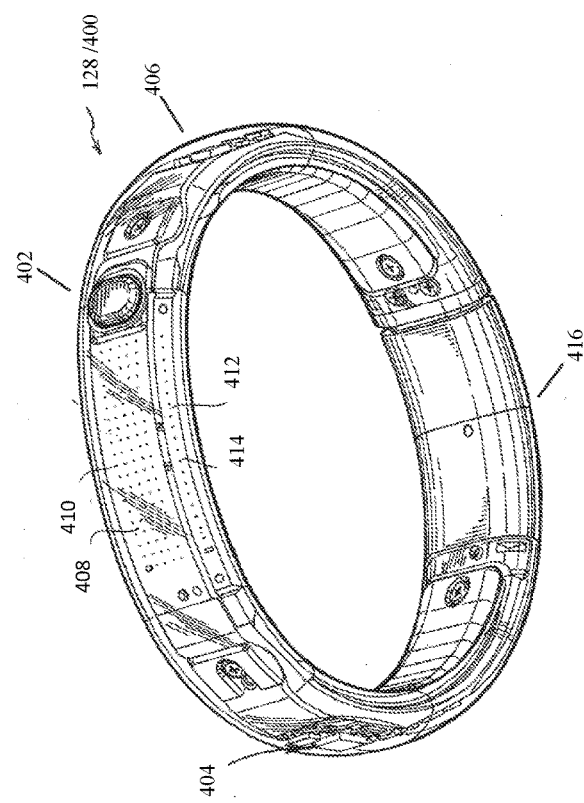
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing/athletic apparel. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
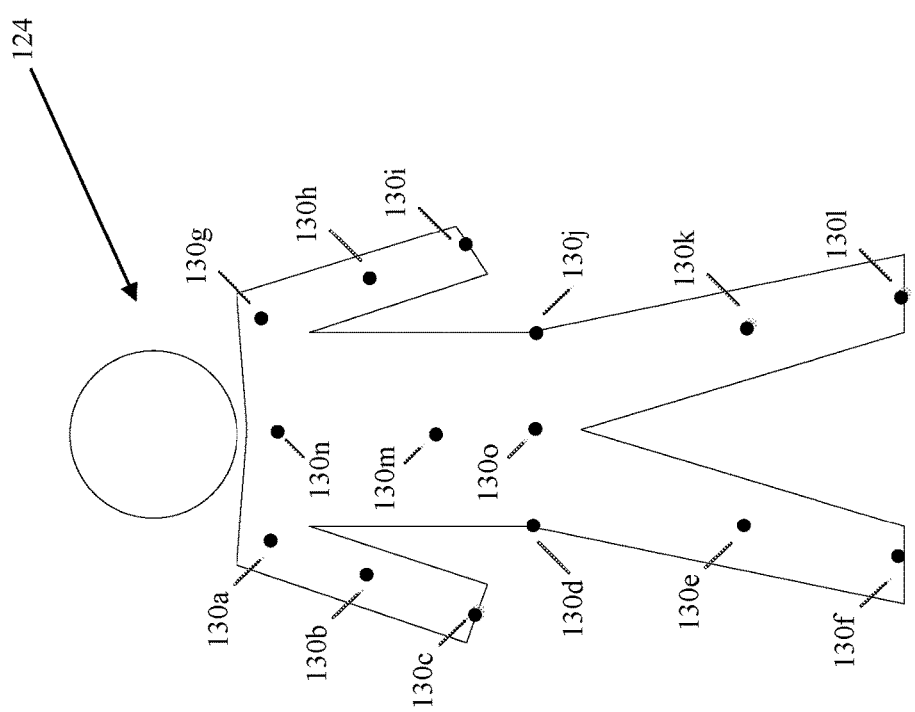
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 1306n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple sensor locations, such as sensors 130m-130o, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130m-130o may serve as a point for a center of moment location of user 124. In another embodiment, one or more locations may serve as a center of moment of specific body parts or regions.

Aspects of the innovation relate to energy harvesting devices (otherwise referred to as energy capture devices, or energy capture and storage devices), and novel methods of utilizing one or more energy harvesting devices. Advantageously, aspects of the innovations described herein relate to using a thermoelectric generator to provide electrical energy to one or more electronic components of an athletic activity monitoring device (e.g. devices 128, 400), among others. In this way, one or more electronic components (e.g. processor, memory, transceiver, among others) may be provided with electrical energy without requiring a user to provide an energy storage device/medium, such as a battery, with a wired source of electrical energy, such as from an electrical outlet (i.e. a wired connected may not be required for recharging of one or more on-board batteries of an athletic activity monitoring device). In one implementation, one or more thermoelectric generator modules configured to be utilized within an energy harvesting device may generate electrical energy in response to a thermal gradient, and without using an energy storage device or medium (i.e. without a body, or a store of phase change material, among others). In one example, one or more energy harvesting devices may be incorporated into an item of athletic apparel of a user, and such that heat energy may be stored as the item of athletic apparel is laundered. This heat energy may subsequently be used to generate electrical energy using one or more thermoelectric generator modules, as described in the following disclosures. As such, a device incorporating a thermoelectric generator module, as described herein, may not include additional elements for energy storage (i.e. may not include a battery, otherwise referred to as an axillary energy storage medium). In another example, a device that incorporates a thermoelectric generator module, such as those described herein, may utilize a hybrid of, among others, battery storage, in additional to generating electrical energy using a thermoelectric generator module.

FIG. 6 depicts exemplary thermal harvesting devices according to example embodiments disclosed herein. In one example FIG. 6A schematically depicts one implementation of an energy harvesting device 600, according to one or more aspects described herein. In one example, the energy harvesting device 600 may be configured to be positioned within an item of clothing, and may be configured to absorb and store heat energy from one or more of a wash and dry cycle as the item of clothing is being laundered. In certain embodiments, the device 600 may be configured to be irremovably positioned within an item, such as clothing. For example, a user may wear an article of clothing having the device 600 positioned in a first location within a garment or article, and the device remains at the first location during cleaning and/or storage of the garment or article, such as in between subsequent uses or wear. In various implementations, the laundering of the device 600 and/or wearing of the device 600 during athletic activity, store absorbed heat energy, which may be used to generate electrical energy using a thermoelectric generator, such as thermoelectric generator 622.

In one implementation, the energy harvesting device 600 may comprise an insulated container, otherwise referred to as a container structure. For example, in certain embodiments, one or more insulated containers may form an outer casing of the device 600 (See, e.g., insulated container 602). An insulated container, e.g., container 602, may form the outer-most perimeter or layer or device 600. An insulated container 602 may further comprise an outer membrane 604 that has an outer surface 606 and an inner surface 608. The insulated container 602 may further comprise an inner membrane 610 that is spaced apart, in terms of an outer periphery of the device 600, from the outer membrane 604. In turn, the example inner membrane 610 is shown having an outer surface 612, and an inner surface 614. An outer cavity 616 may be spaced between the outer membrane 604 and the inner membrane 610. An aperture 618 may extend from the outer surface 606 of the outer membrane 604 to the inner surface 608 of the outer membrane 604. The aperture 618 may be configured to permit ingress and egress of a gas and/or fluid, such as for example, air and/or water, or another fluid, from and to an external environment (represented by reference numeral 601).

The energy harvesting device 600 may comprise an inner cavity 620 encapsulated by the inner membrane 610. An outer heat exchanger 624 may extend through the inner membrane 610. A thermoelectric generator 622 may be positioned within the inner cavity 620. The thermoelectric generator 622 may be thermally-coupled to the outer heat exchanger 624 at a first side 621 and to an inner heat exchanger 626 at a second side 623. An expandable membrane 628, otherwise referred herein as an expandable bladder 628, may encapsulate a mass of phase-change material 630, and at least a portion of the expandable membrane 628 may be coupled to the inner heat exchanger 626. Accordingly, the outer heat exchanger 624, the thermoelectric generator 622, and the inner heat exchanger 626 may be configured to allow bi-directional conduction of heat energy between the phase-change material 630 and the external environment 601 (i.e., conduction into or out from the phase-change material 630). In one example, the outer heat exchanger 624 may extend through the inner membrane 610. As such, a portion of the inner membrane 610 may be sealed around at least a portion of the outer heat exchanger 624.

In one example, the outer membrane 604 of the insulated container 602 may comprise a polymer that is impermeable to air and water, and/or impermeable to one or more additional fluids (e.g. one or more organic or synthetic oils, and/or one or more of nitrogen gas or helium gas, among many others). In certain embodiments, the outer membrane 604 may be formed such that the structure of the outer membrane 604 is configured to be rigid during use of the device 600. In another example, the outer membrane 604 may be configured to be deformable during use of the device 600. In yet further embodiments, the outer membrane 604 may be rigid in a first configuration, however, become more pliable or flexible in a second configuration, which may be automatically transitioned between in at least one intended use situation. In various implementations, the outer membrane 604 (and/or any other membrane disclosed herein) may comprise one or more of polyethylene, polypropylene, polyvinyl chloride, polystyrene, polycarbonate, polyurethane, polymethylmethacrylate, polyethylene terephthalate, para-aramid, polychlorotrifluoroethylene, polyamide, polychloroprene, polyester, polyimide, phenol-formaldehyde resin, polyacrylonitrile, among other polymers. As such, the outer membrane 604 may comprise one or more synthetic rubber materials, including styrene-butadiene rubbers as well as rubbers utilizing isoprene, chloroprene, and isobutylene. Additionally or alternatively, the outer membrane 604 may comprise one or more ceramics, fiber-reinforced materials, metals or alloys, or combinations thereof.

The inner membrane 610 of the insulated container 602 may comprise a same material, or combination of materials, as the outer membrane 604. Accordingly, the inner membrane 610 may be impermeable to air, water and/or one or more additional fluids. In one example, the inner membrane 610 may be configured to be rigid and maintain a consistent geometry during use of the device 600. In another example, the inner membrane 610 may be configured to deform during use of device 600. As discussed above in reference to the outer membrane 604, the inner membrane 610 may be transitioned between at least two configurations in which the rigidity is altered. In certain implementations, the inner membrane 610 may comprise a different material, or materials, to the outer membrane 604, and including one or more of the materials disclosed herein or generally known in the art.

The phase-change material 630 may be configured to store thermal energy (a.k.a. heat energy) by absorbing, in one example, an amount of energy corresponding to a latent heat energy for fusion (or specific latent heat for fusion) for a given phase-change material 630 in order to change a state of the phase-change material 630 from a solid to a liquid. It is noted that additional energy may be absorbed and stored by the phase-change material 630 in order to raise a temperature of the phase-change material (additional energy absorbed and stored by the phase-change material 630 may correspond to a heat capacity (or specific heat capacity) of the phase-change material 630).

In one implementation, an amount of energy stored by a phase-change material 630 (otherwise referred to as "PCM" 630) that is initially at a temperature T1 (Kelvin), heated to a temperature T2 (Kelvin), and having a melting temperature Tm (Kelvin), with T1<Tm<T2 is given by:

Energy stored [J]=(Tm−T1)[K]*(specific heat capacity of PCM in solid phase)[J/kg·K]*(mass of PCM)[kg]+(specific latent heat of fusion)[J/kg]*(mass of PCM)[kg]+(T2−Tm)[K]*(specific heat capacity of PCM in liquid phase)[J/kg·K]*(mass of PCM)[kg]   (Equation 1)

The phase-change material 630 may comprise a salt-hydrate based material of the general form $M_n.H_2O$, where M generally represents a metal atom or compound, and n is an integer. In one example, the phase-change material 630 may comprise sodium sulfate; $Na_2.SO_4.10H_2O$. In another example, the phase-change material 630 may comprise $NaCl.Na_2.SO_4.10H_2O$. However, additional or alternative phase-change materials may be utilized with the energy harvesting device 600. In one example, a specific phase-change material may be selected for use with the energy harvesting device 600 based upon an expected temperature range to which the energy harvesting device 600 may be exposed. As such, the phase-change material 630 may be selected to have a melting temperature within the temperature range to which the energy harvesting device 600 is expected to be exposed under one or more intended use conditions.

In one example, the energy harvesting device 600 may be configured to store heat energy when a mean environmental temperature of the external environment 601 is above a mean temperature of the phase-change material 630, and configured to reject heat to the external environment 601 when the mean environmental temperature of the external environment 601 is below a mean temperature of the phase-change material 630. In one example, the energy harvesting device 600 may be configured to be exposed to the external environment 601 having a "mean cool temperature" (e.g. the temperature threshold in which . . . ) in the range of approximately −30° C. to approximately 45° C. In another example, the mean cool temperature may be in the range of approximately −10° C. to approximately 35° C., approximately 0° C. to approximately 30° C., approximately 10° C. to 25° C., or approximately 20° C. to 25° C. In yet another example, the mean cool temperature may be approximately 0° C., approximately 20° C., approximately 21° C., or approximately 25° C. In this way, the mean cool temperature may correspond to a prevailing atmospheric temperature when the external environment 601 corresponds to an outdoor temperature, or to a room temperature, among others. Additionally, the energy harvesting device 600 may be configured to be exposed to an external environment 601 having a "mean hot temperature" in the range of approximately 35° C. to approximately 105° C. In another example, the mean hot temperature may be in the range of approximately 40° C. to a prop 95° C., 45° C. to approximately 85° C., approximately 50° C. to approximately 80° C., or approximately 55° C. to approximately 75° C. In this way, the mean hot temperature may correspond to a prevailing atmospheric temperature when the external environment 601 corresponds to a "warm" or "hot" cycle of a wash cycle in a laundry (washing) machine (or combined "washer-dryer machine"), or a dryer cycle in a laundry (dryer) machine (or combined "washer-dryer machine").

Additional or alternative environments configured to expose the energy harvesting device 600 to the described mean hot temperature may be utilized. For example, the energy harvesting device 600 may be configured to absorb heat energy from any external environment 601 having a mean temperature above a mean temperature of the phase-change material 630. These additional or alternative environments may include a shower, a bath, or a sink environment, such that the energy harvesting device 600 may absorb a portion of energy associated with hot water from a shower, or a water-filled bath or sink. E.g. the energy harvesting device 600 may be brought into direct contact with hot water associated with a shower, bath, or a sink. In another example, the energy harvesting device 600 may absorb a portion of energy associated with a hot beverage (i.e. the energy harvesting device 600 may be submerged into the hot beverage, or may be placed in close proximity to a container storing the hot beverage such that heat may be transferred between the hot beverage and the energy harvesting device 600. In yet another embodiment, sweat from an athlete may be an energy source in terms of thermal energy to be absorbed. In another example, the energy harvesting device 600 may absorb a portion of energy associated with one or more home appliances. For example, the energy harvesting device 600 may absorb a portion of heat energy associated with one or more light bulbs (e.g., energy harvesting device 600 may be positioned in close proximity to a light bulb emitting light energy as well as an amount of heat energy. In another example, the energy harvesting device 600 may absorb a portion of heat energy associated with a home heating appliance (e.g. energy harvesting device 600 may be positioned in close proximity to a hot air vent, or a convection heater, among others). In yet another example, the energy harvesting device 600 may be configured to absorb a portion of heat energy from a human body, either dry and/or wet, such as from perspiration, after a shower, or rain. In one example, the energy harvesting device 600 may be positioned proximate an exposed area of skin of the user, or may absorb a portion of heat energy from a user's body through one or more intermediate layers of clothing and/or equipment. In one embodiment, a user-worn energy harvesting device 600 may allow the gradient from the user's body to the ambient air to serve as an energy source.

The phase-change material 630 may be encapsulated within the expandable membrane 628. As such, the expandable membrane 628 may comprise one or more polymer materials, similar to those polymers described in relation to the outer membrane 604. In one example, one or more fluid-filled bladders may be utilized. Fluid filled bladder members are commonly referred to as "air bladders," and the fluid is often a gas which is commonly referred to as "air" without intending any limitation as to the actual gas composition used. Thus, as used herein, liquid or non-liquid substances may be utilized.

Any suitable components may be used for bladders or otherwise serve as membranes. Regarding the materials for all or various portions of the bladders disclosed herein (e.g., the top and bottom barrier sheets, sidewalls elements and inner barrier layers) may be formed from the same or different barrier materials, such as thermoplastic elastomer films, using known methods. Thermoplastic elastomer films that can be used with the present invention include polyester polyurethane, polyether polyurethane, such as a cast or extruded ester based polyurethane film having a shore "A" hardness of 80 95, e.g., Tetra Plastics TPW-250. Other suitable materials can be used such as those disclosed in U.S. Pat. No. 4,183,156 to Rudy, hereby incorporated by reference in its entirety. Among the numerous thermoplastic urethanes which are particularly useful in forming the film layers are urethanes such as Pellethane™, (a trademarked product of the Dow Chemical Company of Midland, Mich.), Elastollan® (a registered trademark of the BASF Corporation) and ESTANE® (a registered trademark of the B.F.

Goodrich Co.), all of which are either ester or ether based. Thermoplastic urethanes based on polyesters, polyethers, polycaprolactone and polycarbonate macrogels can also be employed. Further suitable materials could include thermoplastic films containing crystalline material, such as disclosed in U.S. Pat. Nos. 4,936,029 and/or 5,042,176 to Rudy, which are incorporated by reference in their entirety; polyurethane including a polyester polypol, such as disclosed in U.S. Pat. No. 6,013,340 to Bonk et al., which is incorporated by reference in its entirety; or multi-layer film formed of at least one elastomeric thermoplastic material layer and a barrier material layer formed of a copolymer of ethylene and vinyl alcohol, such as disclosed in U.S. Pat. No. 5,952,065 to Mitchell et al., which is incorporated by reference in its entirety.

In accordance with the present invention, the multiple film layer bladder can be formed with barrier materials that meet the specific needs or specifications of each of its parts. The present invention allows for top layer to be formed of a first barrier material, bottom layer to be formed of a second barrier material and each part of the sidewall(s) to be formed of a third barrier material. Also, the sidewall parts can each be formed of different barrier materials. As discussed above, the inner barrier sheets and the sidewall parts are formed of the same barrier material when the inverted seam is formed by attaching the terminal ends of inner barrier sheets to the outer barrier sheets adjacent a weld of the inner sheets. As a result, when the inner barrier sheets are formed of a different material than outer barrier sheets, the sidewalls are formed of the same material as the inner barrier sheet material. Also, when the inner barrier sheets are formed of different materials, sidewall parts must be are formed of different materials as well for compatibility.

In certain embodiments, modified or unmodified bladders historically utilized to provide cushioning in footwear may be utilized. One well known type of bladder used in footwear is commonly referred to as a "two film bladder." These bladders may include an outer shell formed by welding the peripheral edges of two symmetric pieces of a barrier material together. This results in the top, bottom and sidewalls of the bladder being formed of the same barrier material. In yet other embodiments, a plurality of materials and/or components may form portions of a bladder.

The inventors have discovered that not only can certain bladders provide cushioning, but also may provide a flexible, non-permeable container that allows thermal expansion of one or more phase change materials. Regarding cushioning, in certain embodiments, one of the advantages of gas filled bladders is that gas as a cushioning compound is generally more energy efficient than closed-cell foam. In certain embodiments, one or more bladders may be configured to spread an impact force over a longer period of time, resulting in a smaller impact force being transmitted to the wearer's body.

In various embodiments, one or more bladders (which may comprise one or more phase-change materials) include a tensile member to ensure a fixed, resting relation between the top and bottom barrier layers when the bladder is fully filled, and which often is in a state of tension while acting as a restraining means to maintain the general external form of the bladder. Some example constructions may include composite structures of bladders containing foam or fabric tensile members. One type of such composite construction prior art concerns bladders employing an open-celled foam core as disclosed in U.S. Pat. Nos. 4,874,640 and 5,235,715 to Donzis, which is disclosed herein by reference in its entirety.

Another type of composite construction prior art that may be used in certain embodiments, concerns air bladders which employ three dimensional fabric as tensile members such as those disclosed in U.S. Pat. Nos. 4,906,502 and 5,083,361 to Rudy, which is hereby incorporated by reference in its entirety. The bladders described in the Rudy patents have enjoyed considerable commercial success in NIKE, Inc. brand footwear under the name Tensile-Air® and Zoom™. Bladders using fabric tensile members virtually eliminate deep peaks and valleys, and the methods described in the Rudy patents have proven to provide an excellent bond between the tensile fibers and barrier layers. In addition, the individual tensile fibers are small and deflect easily under load so that the fabric does not interfere with the cushioning properties of air. Those skilled in the art will readily appreciate that these are mere examples and that other structures and implementations are within the scope of this disclosure.

A portion of the expandable membrane 628 may be thermally-coupled to an inner side 627 of the inner heat exchanger 626. At least a portion, which may be another portion of the expandable membrane 628, may be configured to deform and expand in response to a thermal expansion of the phase-change material 630. This expansion of the expandable membrane 628 may be limited by the boundaries of the inner cavity 620, as defined by the inner membrane 610.

In one example, the outer heat exchanger 624 and the inner heat exchanger 626 may comprise one or more metals or alloys with high thermal conductivity values. In one implementation, the outer heat exchanger 624 of the inner heat exchanger 626 may comprise plate geometries. In one implementation, one or more of the outer heat exchanger 624 and the inner heat exchanger 626 may comprise a copper alloy. Additionally or alternatively, one or more of the outer heat exchanger 624 and the inner heat exchanger 626 may comprise an aluminum alloy. In one specific example, one or more of the outer heat exchanger 624 and the inner heat exchanger 626 may comprise aluminum alloy 1050A, aluminum alloy 6061 or aluminum alloy 6063, among others.

The thermoelectric generator 622 may be configured to generate electrical energy in response to a thermal gradient being applied across the device (i.e. to generate electrical energy in response to a gradient being applied between the first side 621 and the second side 623 of the thermoelectric generator 622). In one example, a value of a voltage output from the thermoelectric generator may be directly proportional to a thermal gradient (temperature difference) across the device 622 (between the first side 621 and the second side 623). In one implementation, the thermoelectric generator 622 may comprise highly doped semiconductor materials configured to output a voltage as a result of the Seebeck effect. In one example, a polarity of an output voltage from the thermoelectric generator 622 may depend on the direction of heat transfer through the thermoelectric generator 622. For example, when heat is transferred from the phase-change material 630 through the thermoelectric generator 622 and out to the external environment 601, an output voltage from the thermoelectric generator 622 may have a first polarity. In another example, when heat is transferred from the external environment 601 through the thermoelectric generator 622, and into the phase-change material 630, an output voltage from the thermoelectric generator 622 may have a second polarity, opposite the first polarity. Accordingly, the thermoelectric generator 622 may be configured with one or more electrical circuits configured to condition (rectify) an output voltage to have a same polarity as heat is transferred into, or out from, and the phase-change material 630. Further details of this voltage conditioning are discussed in relation to FIG. 22.

In one example, the thermoelectric generator 622 may be configured to provide electrical energy to one or more devices. Accordingly, the thermoelectric generator 622, as schematically depicted in FIG. 6A, may represent one or more electrical components in addition to the thermoelectric generator itself. Further details of these one or more electrical components in addition to the thermoelectric generator are discussed FIG. 22.

In one example, the phase-change material 630 may be configured to store approximately 0.1 J to 200 J of energy captured from the external environment 601 when the external environment 601 is at a higher temperature than a temperature of the phase-change material 630. Accordingly, as the energy harvesting device 600 is storing energy, a gradient across the thermoelectric generator 622 (with the first side 621 at a higher temperature than the second side 623) may cause the thermoelectric generator 622 to generate a first amount of electrical energy. When exposed to a cooler external environment 601 than the phase-change material 630, the energy harvesting device 600 may be configured to generate a second amount of electrical energy as a result of a thermal gradient across the thermoelectric generator 622 (with the second side 623 at a higher temperature than the first side 621). In one example, the phase-change material 630 may be configured to reach an approximate thermal equilibrium (reach an approximately same temperature) with the external environment 601 at approximately 10° C., 15° C., 20° C., 21° C., 25° C., or in the range of approximately 5 to 10° C., approximately 10 to 25° C., approximately 15 to 25° C., approximately 20 to 25° C., or approximately 25 to 40° C. In one implementation, the phase-change material 630 may be configured to reach an approximate thermal equilibrium with the external environment 601 within at least approximately: 1 hour, 2 hours, 3 hours, 4 hours, 5 hours, 6 hours, 7 hours, 8 hours, 9 hours, 10 hours, 11 hours, 12 hours, 15 hours, 20 hours, 24 hours, 1.5 days, 2 days, three days, four days, five days, 6 days, 7 days, 8 days, 9 days, 10 days, 14 days, or 21 days, among others. In another implementation, the phase-change material 630 may be configured to reach an approximate thermal equilibrium with the external environment 601 within at least approximately 1 to 3 hours, 3 to 6 hours, 6 to 9 hours, 9 to 12 hours, 12 to 24 hours, 1 to 2 days, 2 to 3 days, 3 to 5 days, 5 to 8 days, 8 to 16 days, among others.

Certain embodiments may be configured to not reach equilibrium within a certain intended time frame under certain intended use conditions. The time frame may be as any time frame referenced above or any other time frame. This may be advantageous, in certain embodiments, to regulate thermal energy transfer in a device intended or expected to be within an external environment for an expected threshold quantity of time. For example, one embodiment may require at least 1 hour at a threshold temperature range to reach thermal equilibrium to ensure certain electronic components within the device are heated/cooled at or below a rate and/or do not reach a threshold temperature level within that time that would result in a likelihood of damage to components within the device, such as electronic components. Further, in certain embodiments, the device may be made smaller or with fewer components if it can be exposed to longer periods of thermal energy of certain intensity/intensities. As one specific example, a device that is embedded or intended to be imbedded in articles of clothing or washable textiles may be configured to reach thermal equilibrium towards the latter end of the expected time frame of a wash and/or dry cycle. In certain embodiments, this may be referred to as a failure temperature (discussed in more detail below). Yet, temperatures may fluctuate, therefore, the overall energy transfer rate or cumulative energy transfer may be considered to calculate or determine a failure exposure condition.

In another example, the energy harvesting device 600 may have a storage efficiency of at least 50%, at least 60%, at least 70%, at least 80%, at least 90%, ranging from 60 to 80%, or ranging from 50 to 90% over a timescale during which the energy harvesting device 600 may be configured to reach a thermal equilibrium with the external environment 601, as described above. In this way, a storage efficiency may refer to a percentage of heat energy stored within the phase-change material 630 that transfers through the thermoelectric generator 622. The remaining heat energy initially stored within the phase-change material 630 may be lost to the external environment 601 through one or more alternative heat transfer paths through the energy harvesting device 600 (without passing through the thermoelectric generator 622). This heat loss percentage may be referred to as parasitic heat loss.

In one example, the thermoelectric generator 622 may have a conversion efficiency of approximately 5 to 8%. In another example, the thermoelectric generator 622 may have a conversion efficiency of approximately 1 to 6%, 7 to 10%, or 9 to 12%. This conversion efficiency may represent an amount of electrical energy generated as a percentage of the heat energy stored within the energy harvesting device 600, or as a percentage of the heat energy stored within the energy harvesting device 600 that passes through the thermoelectric generator 622 rather than being lost to the external environment 601 by parasitic heat loss.

In one implementation, the energy harvesting device 600, and in particular, the thermoelectric generator 622, may be configured to output a voltage in a range of 0.01 V to 12 V. In certain examples, the thermoelectric generator 622 may be configured to output a voltage of 0.01 V, 0.02 V, 0.05 V, 0.1 V, 0.15 V, 0.25 V, 0.5 V, 0.75 V, 0.9 V, 1 V, 1.1 V, 1.2 V, 1.5 V, 1.7 V, 1.75 V, 1.9V, 2.0 V, 2.5 V, 3.7V, 5 V, 9 V, 9.9 V, or 10 V, among others. In one implementation, the energy harvesting device 600 may be configured to generate an amount of electrical energy over the timescale during which the phase-change material 630 is configured to reach thermal equilibrium with the external environment 601, as previously discussed. As such, this amount of electrical energy may range from 0.01 mAh to 200 mAh, among others.

In one implementation, one or more elements provided with electrical energy by a thermoelectric generator, such as thermoelectric generator 622 of energy harvesting device 600 may be configured to consume electrical energy (during average use) at a rate range from 1 microwatts to 1000 microwatts. However, additional energy consumption ranges may be utilized, without departing from the disclosures described herein.

The energy harvesting device 600 may be configured to transfer heat substantially along axis 629. Accordingly, axis 629 may be referred to as a primary axis of conduction 629 of the insulated container 602. As such, axis 629 may align with an approximate direction of heat transfer through the outer heat exchanger 624, the thermoelectric generator 622, the inner heat exchanger 626 and the phase-change material 630. In one implementation, the aperture 618 may be aligned with the axis 629. In one example, axis 629 may represent an approximate path of least thermal resistance through the energy harvesting device 600, and such that alternative directions of heat transfer from and to the phase-change material 630 are associated with higher thermal resistances. In one implementation, the inner cavity 620 may provide insulation to the phase-change material 630 such that a first direction along axis 629 represents an approximate direction of least thermal resistance. The inner cavity 620 may be sealed by the inner membrane 610, and comprise an insulating material 625. In one implementation, the insulating material 625 may comprise a mass of air. The insulating material 625 may comprise a mass of another gas, such as, for example, argon, nitrogen, oxygen, carbon dioxide, among others. The insulating material may, additionally or alternatively, comprise a polymer, such as an insulating foam. In certain specific examples, the insulating material 625 may comprise fiberglass, polyurethane, polystyrene, or polyethylene, among others. In another implementation, the inner cavity 620 may comprise a vacuum, or a vacuum chamber.

In one implementation, in order to reduce heat transfer into or out from the energy harvesting device 600 in a direction other than a first direction substantially along axis 629, one or more of the inner surface of the inner membrane 614, the outer surface of the inner membrane 612, the inner surface of the outer membrane 608, and/or the outer surface of the outer membrane 606 may comprise a low emissivity/high reflectivity coating to reduce heat transfer by radiation. As such, any low emissivity coating known in the art may be utilized.

It is noted that FIG. 6A is merely a schematic representation of the energy harvesting device 600. As such, none of the depicted elements of FIG. 6A should be construed as limiting the energy harvesting device 600 to any specific geometries. For example, the circular geometries of the inner membrane 610 and the outer membrane 604 should not be construed as limiting the energy harvesting device 600 to having a circular configuration. As such, the energy harvesting device 600 may be embodied with substantially rectangular or square geometries, without departing from the scope of these disclosures.

In one example, FIG. 6A schematically depicts the energy harvesting device 600 in a first configuration having the outer cavity 616 filled with a mass of air 632. As such, the mass of air 632 may enter into the outer cavity 616 through the aperture 618 from the external environment 601. In this way, the mass of air 632 may act as a thermal barrier (a layer of insulation) between the inner membrane 610, and the external environment 601.

FIG. 6B schematically depicts a second configuration of the energy harvesting device 600, according to one or more aspects described herein. In particular, FIG. 6B schematically depicts the energy harvesting device 600 having a mass of water 634 within the outer cavity 616. The mass of water 634 may enter into the outer cavity 616 through the aperture 618. Further, the mass of air 632 may be partially or wholly displaced out from the outer cavity 616 through the aperture 618 as the water 634 is entering into the outer cavity 616. In one example, the outer cavity 616 may expand upon being filled with a mass of water 634. The device 600 may be configured to allow a certain mass or volume of fluid (e.g., water) to enter during an intended wash cycle. In one implementation, the mass of water 634 may enter into the outer cavity 616 during a wash cycle while the energy harvesting device 600 is positioned within the washing machine (i.e. the external environment 601 may comprise a mass of water within a washing machine). As such, the mass of water 634 may enter into the outer cavity 616 during a wash cycle as an item of clothing within which the energy harvesting device 600 is positioned, is laundered. In one example, upon entering the external environment, the mass of water 634 may have a mean temperature that is higher than the mean temperature of the phase-change material 630. As such, heat may be transferred through the outer heat exchanger 624, the thermoelectric generator 622, and the inner heat exchanger 626 into the phase-change material 630.

In one example, a mass of water 634 retained within the outer cavity 616 of the energy harvesting device 600 may prevent the thermoelectric generator 622, as well as one or more additional electronic components powered by the thermoelectric generator 622, from being exposed to a temperature above a failure temperature. As such, a failure temperature may be a temperature at or above which one or more of the thermoelectric generator 622, or one or more electronic components powered by the thermoelectric generator 622 within the inner cavity 620, may experience partial or catastrophic failure. In particular, the mass of water 634 may prevent the thermoelectric generator 622 from being exposed to a temperature above a failure temperature by absorbing a portion of heat energy associated with, in one example, a dryer cycle as an item of clothing, textile or other object within which the energy harvesting device 600 is retained, is laundered.

In one example, the mass of water 634 may enter into the outer cavity 616 of the energy harvesting device 600 during a wash cycle as an item of clothing, within which the energy harvesting device 600 is located, is laundered. Subsequently, the item of clothing, and in turn, the energy harvesting device 600, may be exposed to a dryer cycle. In one implementation, while progressing through a dryer cycle, the mass of water 634 may absorb a portion of heat energy as the dryer warms the textile, clothing or object, and shield the thermoelectric generator 622, as well as one or more additional electronic components retained within the inner cavity 620, from being exposed to a temperature above a failure temperature or failure time frame (or combinations thereof that form a failure condition). In particular, the water 634 may absorb a portion of heat energy associated with a dryer cycle before evaporating out through the aperture 618.

In one implementation, the outer cavity 616 may be configured such that the mass of water 634 retained within the outer cavity 616 may evaporate, and allow the phase-change material 630 to absorb a design/predetermined amount of heat energy, without exposing the thermoelectric generator 622 to a temperature above a failure temperature, during a predetermined dryer cycle time. In one implementation, the predetermined dryer cycle time may be approximately 15 minutes, 20 minutes, 25 minutes, 30 minutes, 40 minutes, 50 minutes, 60 minutes, 70 minutes, 80 minutes, 90 minutes, 100 minutes, 110 minutes, or 120 minutes, or ranging from approximately 30 to 50 minutes, approximately 50 to 70 minutes, 70 to 90 minutes, or 90 to 120 minutes. In one implementation, the predetermined dryer cycle may be configured to run at a "mean hot temperature," as previously described, which may in certain embodiments be a wide range of temperatures.

In one example, the mass of water 634 may be configured to enter into the outer cavity 616 by capillary action. In another example, the mass of water 634 may be configured to enter into the outer cavity 616 when the energy harvesting device 600 is exposed to one or more turbulence forces associated with a wash cycle of a washing machine. In another example, the mass of water 634 may be configured enter into the outer cavity 616 when a pressure level of the external environment 601 is greater than a pressure within the outer cavity 616 (in one example, a pressure level of the external environment 601 may be greater than a pressure within the outer cavity 616 when the energy harvesting device 600 is submerged below a water surface and the outer cavity 616 contains a mass of air 632). In one implementation, the energy harvesting device 600 containing a mass of air 632, as depicted in FIG. 6A, may have a density of greater than 1 g/cm³. In another implementation, the energy harvesting device 600, as depicted in FIG. 6A containing a mass of air 632 may have a density of less than 1 g/cm³.

Figure 6D:
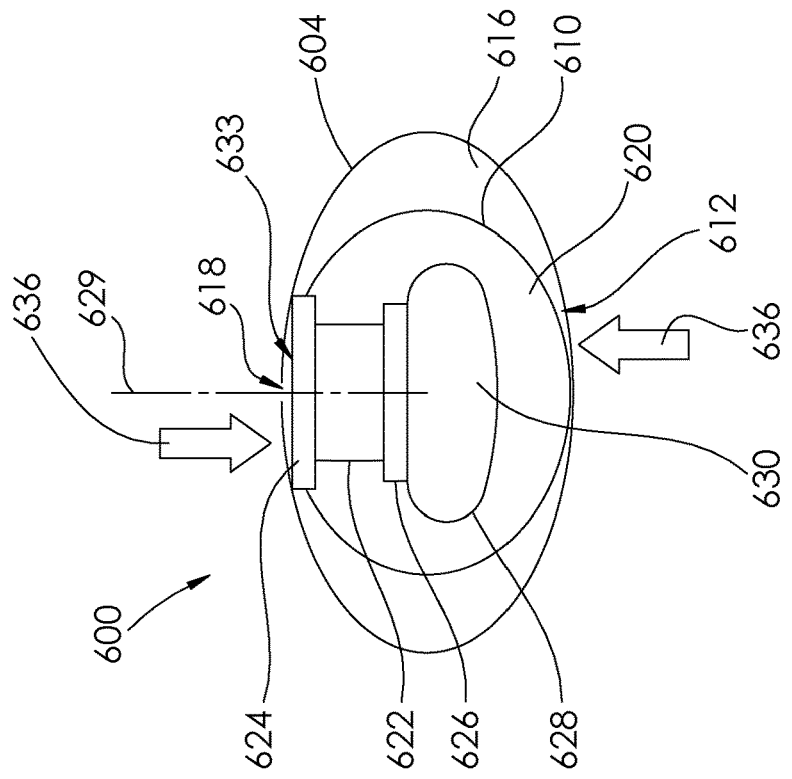
FIG. 6D schematically depicts yet another embodiment of an energy harvesting device, which may be, in certain embodiments, a different configuration of the energy harvesting device depicted in FIG. 6C, and in which an outer membrane may be configured to be compressible when exposed to an external force, according to one or more aspects described herein.
Figure 6C:
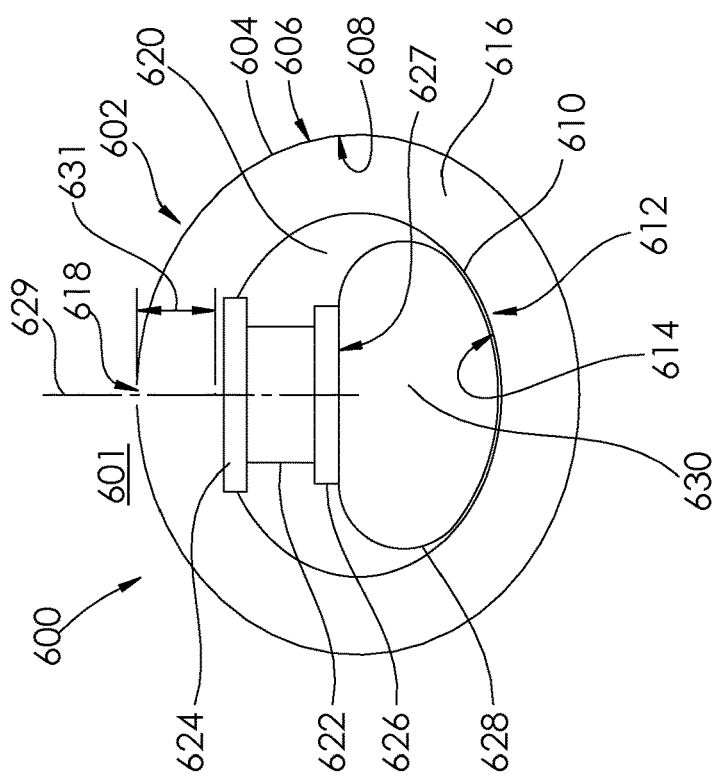
FIG. 6C schematically depicts yet another embodiment of an energy harvesting device, which may, in certain embodiments, be a different configuration of the energy harvesting device depicted in FIG. 6B, and in which an expandable membrane is in an expanded configuration, according to one or more aspects described herein.

FIG. 6C schematically depicts a third configuration of the energy harvesting device 600, according to one or more aspects described herein. In one example, FIG. 6C schematically depicts an expandable membrane, such as membrane 628 of FIG. 6B in a second, expanded configuration. Thus, in certain embodiments FIG. 6B schematically depicts the expandable membrane 628 in a first, contracted configuration, and FIG. 6C schematically depicts the energy harvesting device 600 storing an amount of heat energy within the phase-change material 630. It is noted that when in the expanded configuration depicted in FIG. 6C, a portion of the expandable membrane 628 is retained in a thermal coupling to the inner side 627 of the inner heat exchanger 626.

FIG. 6D schematically depicts an example energy harvesting device, which may be in certain implementations, a fourth configuration of the energy harvesting device 600, according to one or more aspects described herein. As previously discussed, the outer membrane 604 of the energy harvesting device 600 may be deformable (compressible). In one example, the energy harvesting device 600 may be coupled to, or integrally-formed with, an item of clothing. As such, in order to conform to one or more contours of a human user, the outer membrane 604 may be configured to be compressible when exposed to an external force, such as external force 636. In one example, the energy harvesting device 600 may be positioned within the item of clothing or equipment configured to be worn in a tightly-fitted configuration on the user's body. As such, FIG. 6D may schematically represent a compressed configuration resulting from a user putting on the item of clothing or equipment within which the energy harvesting device 600 may be positioned. In this way, the external force 636 may represent a force exerted by the tightly-fitted item of clothing/equipment, and the user's body, on the energy harvesting device 600.

As schematically depicted in FIG. 6D, the external force 636 may be aligned substantially along axis 629. In another implementation, an external force may be exerted substantially along an alternative axis, or may be resolved along two or more axes. However, in one implementation, the energy harvesting device 600 may be configured such that an external force 636 acts substantially along a first direction along axis 629. In one example, the external force 636 may be utilized to reduce a separation distance 631 between the outer membrane 604 and the inner membrane 610. In this way, an amount of insulation provided by the outer cavity 616 between an outer surface 633 of the outer heat exchanger 624 and the external environment 601 may be reduced by compression of the outer membrane 604 due to the external force 636. In this way, by compressing the outer membrane 604 substantially along axis 629, a thermal resistance associated with a conduction pathway through the inner heat exchanger 626, the thermoelectric generator 622, and the outer heat exchanger 624 may be reduced. Accordingly, in accordance with one embodiment, when the outer membrane 604 is in the expanded configuration, as depicted for example, in FIG. 6C (i.e. when, in one example, the energy harvesting device 600 is not being worn by a user), the outer cavity 616 may be configured to provide increased thermal resistance, thereby reducing heat transfer out of the phase-change material 630 (and consequently, reducing electrical energy generation by the thermoelectric generator 622). When the outer membrane 604 is in a compressed configuration, as depicted in FIG. 6D (i.e. when, in one example, the energy harvesting device 600 is being worn by a user), the outer cavity 616 may be configured to provide a decreased thermal resistance, thereby increasing heat transfer out of the phase-change material 630 through the thermoelectric generator 622. As such, the compressive external force 636, when aligned along axis 629, may reconfigure the energy harvesting device 600 into a compressed configuration conducive to generation of electrical energy when it is needed by the user (i.e. when the energy harvesting devices being worn by the user).

FIG. 7A schematically depicts another implementation of an energy harvesting device 700, according to one or more aspects described herein. It is noted that the energy harvesting device 700 may include one or more elements similar to those elements described in relation to energy harvesting device 600 from FIGS. 6A-6D, where similar reference numerals represent similar components and features. The energy harvesting device 700 may be configured with an insulated container 701 having an outer membrane 604 with a plurality of apertures 702a-702i. Accordingly, apertures 702a-702i may represent one implementation of a plurality of apertures extending from the outer surface 606 of the outer membrane 604 to the inner surface 608 of the outer member 604, and greater than or fewer than the depicted apertures 702a-702i may be utilized with the energy harvesting device 700, without departing from the scope of these disclosures.

In one example, FIG. 7A schematically depicts the energy harvesting device 700 in an expanded configuration. In turn, FIG. 7B schematically depicts an energy harvesting device, which may be energy harvesting device 700 of FIG. 7A, in a compressed configuration, similar to that compressed configuration depicted in FIG. 6D. In one example, the apertures 702a-702i may be substantially aligned with the outer surface 633 of the outer heat exchanger 624. As such, when in the compressed configuration of FIG. 7B, the plurality of apertures 702a-702i may be substantially proximate the outer surface 633 of the outer heat exchanger 624.

FIG. 8 schematically depicts another implementation of an energy harvesting device 800, according to one or more aspects described herein. Accordingly, the energy harvesting device 800 may include one or more elements similar to those elements described in relation to energy harvesting devices 600 and 700 (or any other energy harvesting device disclosed herein), where similar reference numerals represent similar components and features. The energy harvesting device 800 may be configured with an insulated container 802, the insulated container 802 having an outer membrane 604 with a plurality of apertures 804a-804f. Accordingly, apertures 804a-804f may represent one implementation of a plurality of apertures extending from the outer surface 606 of the outer membrane 604 to the inner surface 608 of the outer membrane 604. In one implementation, greater than, or fewer than, the depicted apertures 804a-804f may be utilized with the energy harvesting device 800, without departing from the scope of these disclosures.

In one example, and in contrast to FIG. 7A, the apertures 804a-804f may not be aligned with the outer surface 633 of the outer heat exchanger 624. In one example, the apertures 804a-804f may be positioned on the outer membrane 604 such that when in a compressed configuration, similar to FIG. 7B, the plurality of apertures 804a-804f of the energy harvesting device 800 are not positioned proximate the outer surface 633 of the outer heat exchanger 624. In one example, the plurality of apertures 804a-804f may be positioned beyond axes 808 and 810, where axes 808 and 810, in one example, extend from an approximate center 806 of the energy harvesting device 800 through corners (outermost edges) 818 and 820 of the outer heat exchanger 633. In another example, the plurality of apertures 804a-804f may be positioned beyond axes 812 and 814, where axes 812 and 814, extend approximately parallel to axis 629 from corners 818 and 820 of the outer heat exchanger 633.

FIG. 9 schematically depicts another implementation of an energy harvesting device 900, according to one or more aspects described herein. It is noted that the energy harvesting device 900 may include one or more elements similar to one or more elements described in relation to energy harvesting devices 600, 700 and 800 or any other device described herein, where similar reference numerals represent similar components and features. In one example, an insulated container 902 of the energy harvesting device 900 may comprise a polymeric foam 904 positioned within the outer cavity 616. In one example, the foam 904 may comprise an open-cell (reticulated) foam. In another example, the foam 904 may comprise a closed-cell foam. In specific implementations, foam 904 may comprise one or more of polyurethane foam, polyvinyl chloride foam, Styrofoam, polyimide foam, silicone foam, or microcellular foam, among others. In one implementation, the foam 904 may be configured to absorb a mass of water, similar to the mass of water 634 described in relation to FIG. 6B. In one example, the foam 904 may expand within the outer cavity 616 as a mass of water is absorbed, and contract upon evaporation of the mass of water. Additionally or alternatively, the outer cavity 616 may be configured to retain a mass of air, similar to the mass of air 632, in addition to the foam 904. In certain embodiments, it may be configured to retain a mass or volume or air under one intended use condition and a volume or mass of water under a second intended use condition.

FIG. 10 schematically depicts another implementation of an energy harvesting device 1000, according to one or more aspects described herein. It is noted that the energy harvesting device 1000 may include one or more elements similar to one or more elements described in relation to energy harvesting devices 600, 700 and 800, 900 (and/or any other energy harvesting device disclosed herein), where similar reference numerals represent similar components and features. In one example, the energy harvesting device 1000 may comprise an insulated container 1001 that forms an outer casing of the device 1000. The insulated container 1001 may further comprise an outer membrane 604 that has an outer surface 606 and an inner surface 608. The insulated container 1001 may further comprise an inner membrane 610 having an outer surface 612 and an inner surface 614. An outer cavity 616 may be spaced between the outer membrane 604 and the inner membrane 610. In one implementation, one or more apertures 1008a and 1008b may extend from the outer surface 606 of the outer membrane 604 to the inner surface 608 of the outer membrane 604. The apertures 1008a and 1008b may be configured to permit ingress of air and/or water from an external environment 601. The energy harvesting device 1000 may further comprise an inner cavity 620 encapsulated by the inner membrane 610. A thermoelectric generator 1004 may be positioned within the inner cavity 620. In one example, the thermoelectric generator 1004 may be similar to the thermoelectric generator 622. The thermoelectric generator 1004 may be thermally-coupled to an outer heat exchanger 1002 at a first side 1008, and to an inner heat exchanger 1006 at a second side 1010. In one implementation, the inner heat exchanger 1006 and the thermoelectric generator 1004 may be fully contained within the inner cavity 620. The outer heat exchanger 1002 may, in one example, extend between the inner cavity 620 and the external environment 601. As such, the outer heat exchanger may extend through the inner membrane 610 and the outer membrane 604, such that at least one surface of the outer heat exchanger 1002 is exposed to the inner cavity 620, and at least one surface of the outer heat exchanger 1002 is exposed to the external environment 601. An expandable membrane 628, otherwise referred to as an expandable bladder 628, may encapsulate a mass of phase-change material 630, and at least a portion of the expandable membrane 628 may be thermally-coupled to the inner heat exchanger 1006. Accordingly, the outer heat exchanger 1002, the thermoelectric generator 1004, and the inner heat exchanger 1006 may be configured to allow bi-directional conduction of heat between the phase-change material 630, and the external environment 601. In one example, this bi-directional conduction of heat may be substantially along axis 629, otherwise referred to as a primary axis of conduction 629 of the insulated container 1001.

In one example, the one or more apertures 1008a and 1008b of the insulating container 1001 may be positioned on the outer membrane 604 such that the apertures 1008a and 1008b are not substantially aligned along axis 629, and such that heat conduction is primarily through the outer heat exchanger 1002, the thermoelectric generator 1004, the inner heat exchanger 1006, and the phase-change material 630. In yet one embodiment, any of the energy harvesting devices disclosed herein such that an exit point or aperture may be placed such that exiting steam from heated fluid such as water is positioned to provide thermal energy to at least one heat exchanger.

FIG. 11 schematically depicts another implementation of an energy harvesting device 1100, according to one or more aspects described herein. It is noted that the energy harvesting device 1100 may include one or more elements similar to one or more elements described in relation to energy harvesting devices 600, 700, 800, 900 (and/or any energy harvesting device disclosed herein), and 1000, where similar reference numerals represent similar components and features. In one example, the energy harvesting device 1100 may have an insulated container 1102. In one example, the insulating container 1102 may be similar to insulated containers 602, 701, 802, 902, and 1001, as previously described.

The energy harvesting device 1100 may have a permeable outer membrane 1104 (permeable at least to air and/or water) having an outer surface 1006 and an inner surface 1008. As such, an outer cavity 616 of the energy harvesting device 1100 may contain a mass of air 632, and may be configured to allow a mass of water, similar to that mass of water 634 described in relation to FIG. 6B, to displace at least a portion of the mass of air 632 when the energy harvesting device 1100 is exposed to water within the external environment 601.

It will be appreciated that various combinations of the implementations described herein may be realized. For example, the energy harvesting device 1100 may be combined with an open-cell foam, similar to open-cell foam 904, without departing from the scope of these disclosures. In this alternative implementation, the insulated container 1102 may form the outer casing of the device 1100. Insulated container 1102 may further comprise the permeable outer membrane 1104 having an outer surface 1106, and an inner surface 1108. The insulated container 1102 may further comprise an inner membrane 610 that has an outer surface 612 and an inner surface 614. An outer cavity 616 may be spaced between the outer membrane 1104 and the inner membrane 610. This outer cavity 616 may be at least partially filled with open-cell foam, similar to open-cell foam 904, as described in FIG. 9. An inner cavity 620 may be encapsulated by the inner membrane 610. In one implementation, and an outer heat exchanger 624 may extend through the inner membrane 610, such that at least a first surface of the outer heat exchanger 624 is exposed to the outer cavity 616 and at least a second surface of the outer heat exchanger 624 is exposed to the inner cavity 620, or exposed to an element positioned within the inner cavity 620. As such, a thermoelectric generator 622 may be positioned within the inner cavity 620, the thermoelectric generator 622 being thermally-coupled to the outer heat exchanger 624 at a first side 621 and to an inner heat exchanger 626 at a second side 623. Additionally, an expandable membrane 628, otherwise referred to as an expandable bladder 628, may encapsulate a mass of phase-change material 630, and at least a portion of the expandable membrane 628 may be coupled to the inner heat exchanger 626. Furthermore, additional combinations of the described implementations of various energy harvesting devices may be realized, without departing from the scope of these disclosures.

FIG. 12 schematically depicts another implementation of an energy harvesting device 1200, according to one or more aspects described herein. It is noted that energy harvesting device 1200 may include one or more elements similar to one or more elements described in relation to energy harvesting devices 600, 700, 800, 900, 1000, and 1100 (and/or any other energy harvesting device disclosed herein), where similar reference numerals represent similar components and features. In one example, the energy harvesting device 1200 may have an insulated container 1202, which may be similar to insulated container 602, 701, 802, 902, 1001, and 1102, as previously described.

In one implementation, the energy harvesting device 1200 may be configured to allow bi-directional conduction of heat between a phase-change material 630 and an external environment 601 through a thermoelectric generator 1204 (which may be similar to thermoelectric generator 622), and an inner heat exchanger 1206 (which may be similar to the inner heat exchanger 626). As such, the energy harvesting device 1200 may not utilize an outer heat exchanger (such as the outer heat exchanger 624), and such that a fluid within the outer cavity 616 (which may be, among others, a mass of air 632, or a mass of water 634) may conduct heat directly to the thermoelectric generator 1204 at a first side 1208. In this way, a primary axis of conduction associated with the energy harvesting device 1200 may be substantially along axis 629 through the thermoelectric generator 1204, the inner heat exchanger 1206, and through to the expandable membrane 628 encapsulating a mass of phase-change material 630.

Accordingly, in one example, at least a portion of the thermoelectric generator 1204 may extend through the inner membrane 610. As such, the at least a portion of the thermoelectric generator 1204 may extend through an opening in the inner membrane 610. Accordingly, this opening may form a seal around the thermoelectric generator 1204.

FIG. 13 schematically depicts another implementation of an energy harvesting device 1300, according to one or more aspects described herein. It is noted that energy harvesting device 1300 may include one or more elements similar to one or more elements described in relation to energy harvesting devices 600, 700, 800, 900, 1000, 1100, and 1200 (and/or any thermal energy harvesting device disclosed herein), where similar reference numerals represent similar components and features. In one example, the energy harvesting device 1300 may comprise an insulated container 1302, which may be similar to insulated container 602. The insulated container 1302 may further have an outer membrane 1303, similar to outer membrane 604, and an inner membrane 1304, similar to inner membrane 610. An outer cavity 1306 may be spaced between the outer membrane 1303 and the inner membrane 1304. An aperture 1314, similar to aperture 618, may extend from an external environment 601 through to the outer cavity 1306. As such, the aperture 1314 may be configured to permit ingress/egress of air and/or water from/to the external environment 601.

The energy harvesting device 1300 may further comprise an inner cavity 1308, similar to inner cavity 620. The inner cavity 1308 may be encapsulated by the inner membrane 1304. In one example, a thermoelectric generator 1320, similar to thermoelectric generator 622, may be encapsulated within the outer cavity 1306. Accordingly, the thermoelectric generator 1320 may be thermally-coupled to an outer heat exchanger 1322, similar to outer heat exchanger 624, at a first side 1330. Further, the thermoelectric generator 1320 may be thermally-coupled to an inner heat exchanger 1318, similar to inner heat exchanger 626, at a second side 1332. In one example, the inner heat exchanger 1332 may extend across the inner membrane 1304, such that the inner membrane 1304 is sealed around the inner heat exchanger 1318, and the inner heat exchanger 1318 may have at least one surface in contact with the inner cavity 1308, and/or at least one surface in contact with an element positioned within the inner cavity 1308. In one example, a portion of an expandable membrane 1312, similar to expandable membrane 628, may be coupled to the inner heat exchanger 1318, the expandable membrane 1312 encapsulating a mass of phase-change material 1310, similar to that mass of phase-change material 630.

The outer membrane 1303 and the inner membrane 1304 may be substantially impermeable. Accordingly, a mass of air and/or water may enter into the outer cavity 1306 through the aperture 1314 in the outer membrane 1303. In one example, an insulating material 1316 may encapsulate at least a portion of the thermoelectric generator 1320, such that a fluid (which may include, among others, water and/or air) within the outer cavity 1306 does not come into direct contact with the thermoelectric generator 1320. In this regard, the insulating material 1316 may comprise one or more of a polymer, a metal, an alloy or a ceramic, and may include, but is not limited to, any specific material disclosed in this document, or any material known in the art. Further, the insulating material 1316 may be utilized to prevent heat conduction along a non-desirable axis, and such that heat conduction through the inner heat exchanger 1318, the thermoelectric generator 1320, and the outer heat exchanger 1322 is substantially along axis 1334, similar to axis 629. In one implementation, an outer surface 1336 of the outer heat exchanger 1322 may be exposed to the outer cavity 1306.

FIGS. 14A and 14B schematically depict another implementation of an energy harvesting device 1400, according to one or more aspects described herein. It is noted that energy harvesting device 1400 may include one or more elements similar to one or more elements described in relation to energy harvesting devices 600, 700, 800, 900, 1000, 1100, 1200, and 1300 (and/or any other energy harvesting device disclosed herein), where similar reference numerals represent similar components and features. In one example, the energy harvesting device 1400 may be configured to deform, or compress, between an expanded configuration, as depicted in FIG. 14A, and a compressed configuration, as depicted in FIG. 14B.

Accordingly, the energy harvesting device 1400 may comprise an insulated container 1402, which may be similar to insulating container 602. As such, the insulated container 1402 may comprise an outer membrane 604 having an outer surface 606 and an inner surface 608. The insulated container 1402 may further comprise an inner membrane 610 having an outer surface 612 and an inner surface 614. An outer cavity 616 may be spaced between the outer membrane 604 and the inner membrane 610. In one example, an aperture 1410 may extend from the outer surface 606 of the outer membrane 604 to the inner surface 608 of the outer membrane 604. In one implementation, the aperture 1410 may be positioned on the outer membrane 604 such that the aperture 1410 is not substantially aligned with a primary conduction axis 1412 of the energy harvesting device 1400. This aperture 1410 may be configured to permit ingress and egress of air and/or water from and to an external environment 601. The energy harvesting device 1400 may further comprise an inner cavity 620 encapsulated by the inner membrane 610.

In one implementation, the energy harvesting device 1400 may comprise an outer heat exchanger 1404 extending through the outer membrane 604. Accordingly, in the expanded configuration depicted in FIG. 14A, the outer heat exchanger 1404 may have an outer surface 1414 exposed to the external environment 601, and an inner surface 1416 exposed to the outer cavity 616. As such, in the expanded configuration of FIG. 14A, the inner surface 1416 of the outer heat exchanger 1404 may be spaced apart from an outer surface 1418 of a thermoelectric generator 1406. In one example, the thermoelectric generator 1406 may be similar to the thermoelectric generator 622. The thermoelectric generator 1406 may be positioned within the inner cavity 620, and have at least a portion extending through the inner membrane 610 such that the outer surface 1418 is exposed to the outer cavity 616. As such, in the expanded configuration schematically depicted in FIG. 14A, the inner surface 1416 of the outer heat exchanger 1404, may be spaced apart from the outer surface 1418 of the thermoelectric generator 1406.

The thermoelectric generator 1406 may be thermally-coupled to an inner heat exchanger 1408, similar to inner heat exchanger 626, at an inner surface 1420. In turn, an expandable membrane 628 may encapsulate a mass of phase-change material 630, and such that at least a portion of the expandable membrane 628 may be coupled to the inner heat exchanger 1408.

An expanded configuration of the energy harvesting device 1400, as depicted in FIG. 14A, may include a separation distance 1422 between the inner surface 1416 of the outer heat exchanger 1404, and the outer surface 1418 of the thermoelectric generator 1406. When transitioned into a compressed configuration, as schematically depicted in FIG. 14B, this separation distance 1422 may be reduced to approximately zero, such that the inner surface 1416 of the outer heat exchanger 1404 is positioned proximate to the outer surface 1418 of the thermoelectric generator 1406. In one example, an external force 1411 applied substantially parallel to axis 1412 may compress the energy harvesting device 1400, thereby urging the outer heat exchanger 1414 towards the thermoelectric generator 1406. As such, when in the compressed configuration, as depicted in FIG. 14B, a thermal resistance along axis 1412 may be reduced (in one example, a thermal resistance may be reduced by reducing the separation between the outer heat exchanger 1404 and the thermoelectric generator 1406).

In one example, when in the expanded configuration, as schematically depicted in FIG. 14A, having the outer heat exchanger 1404 spaced apart from the thermoelectric generator 1406, the thermal resistance resulting from the separation distance 1422 may be such that thermal conduction substantially along axis 1412 is below a threshold level of conduction. In turn, an amount of electrical energy generated by the thermoelectric generator 1406 when in the expanded configuration depicted in FIG. 14A may be below a threshold amount of generated electrical energy. Conversely, when the outer heat exchanger 1404 is brought into contact with the thermoelectric generator 1406, as schematically depicted by the compressed configuration of the energy harvesting device 1400 of FIG. 14B, heat conduction substantially along axis 1412 may be above the threshold level of heat conduction. In turn, the electrical energy generated by the thermoelectric generator 1406 may be above the threshold amount of generated electrical energy. In one example, this threshold amount of generated electrical energy, which may be monitored as one or more of a voltage or a current, among others, may be used to determine whether or not there is an external force 1411 being applied to the energy harvesting device 1400. As such, an output from the thermoelectric generator 1406 may be used to detect an external force 1411 applied to the energy harvesting device 1400. Additionally, an output from the thermoelectric generator 1406 may be used to detect whether an item of clothing within which the energy harvesting device 1400 is positioned is being worn/utilized by a user (whereby it may be assumed that the external force 1411 may result from compression of the energy harvesting device 1400 between one or more layers of clothing and the user's body while the item of clothing within which the energy harvesting device 1400 is positioned is being worn by the user). As such, the energy harvesting device 1400, when compressed from the expanded configuration, as schematically depicted in FIG. 14A, to the compressed configuration, as schematically depicted in FIG. 14B, may be utilized as a switch device configured to detect an application of an external force 1411 to the energy harvesting device 1400.

FIGS. 15A and 15B schematically depict another implementation of an energy harvesting device 1500, according to one or more aspects described herein. It is noted that energy harvesting device 1500 may include one or more elements similar to one or more elements described in relation to energy harvesting devices 600, 700, 800, 900, 1000, 1100, 1200, 1300, and 1400, (and/or any other energy harvesting device disclosed herein), where similar reference numerals represent similar components and features. In a similar manner to energy harvesting device 1400, the energy harvesting device 1500 may be configured to deform, or compress, between an expanded configuration, as depicted in FIG. 15A, and a compressed configuration, as depicted in FIG. 15B.

Accordingly, the energy harvesting device 1500 may comprise an insulated container 1502, which may be similar to insulated container 602. Further, the energy harvesting device 1500 may comprise an outer heat exchanger 1504, similar to outer heat exchanger 624, coupled to the outer membrane 604. As such, the outer heat exchanger 1504 may extend through the outer membrane 604, with the outer membrane 604 sealed around at least a portion of the outer heat exchanger 1504. The outer heat exchanger 1504 may have an outer surface 1516 exposed to an external environment 601 and an inner surface 1518 that is rigidly and thermally-coupled to a thermoelectric generator 1506 within an outer cavity 616. As such, in an expanded configuration, as schematically depicted in FIG. 15A, there may be a separation distance 1530 between an inner surface 1532 of a thermoelectric generator 1506, similar to thermoelectric generator 622, and an outer surface 1534 of the inner heat exchanger 1508, similar to the inner heat exchanger 626.

The insulated container 1502 of the energy harvesting device 1500 may comprise an aperture 1510, similar to aperture 618. In one example, the aperture 1000 may extend from an outer surface 606 of the outer membrane 604 through to the inner surface 608 of the outer membrane 604. As such, the aperture 1510 may not be positioned substantially along axis 1511, where axis 1511 is substantially aligned along a primary conduction axis through the energy harvesting device 1500, similar to axis 629.

FIG. 15B schematically depicts the energy harvesting device 1500 in a compressed configuration. The energy harvesting device 1500 may be transitioned into the depicted compressed configuration of FIG. 15B by external force 1512, similar to external force 636. When in the compressed configuration of FIG. 15B, the thermoelectric generator 1506 may be positioned proximate the inner heat exchanger 1508, such that the separation distance 1530 is reduced to approximately zero, and such that thermal conduction from the phase-change material 630 through the inner heat exchanger 1508, the thermoelectric generator 5006, and the outer heat exchanger 1504 substantially along axis 1511 may be enhanced.

FIG. 16A and FIG. 16B schematically depict another implementation of an energy harvesting device 1600, according to one or more aspects described herein. It is noted that energy harvesting device 1600 may include one or more elements similar to one or more elements described in relation to energy harvesting devices 600, 700, 800, 900, 1000, 1100, 1200, 1300, 1400, and 1500 (and/or any other energy harvesting device disclosed herein), where similar reference numerals represent similar components and features. In particular, the energy harvesting device 1600 may be similar to energy harvesting device 1400, as schematically depicted in FIG. 14A and FIG. 14B. As such, the energy harvesting device 1600 may have an insulated container 1602, similar to insulating container 1402.

In one implementation, the energy harvesting device 1600 may comprise the insulated container 1602 comprising a deformable outer membrane 604 that has an outer surface 606, and an inner surface 608. The insulated container 1602 may further have a deformable inner membrane 610 that is spaced apart from the deformable outer membrane 604, the deformable inner membrane 610 having an outer surface 612 and an inner surface 614. The energy harvesting device 1600 may further have an outer cavity 1620 spaced between the outer membrane 604 and the inner membrane 610. An inner cavity 620 may be encapsulated by the deformable inner membrane 610. An outer heat exchanger 1604 may be coupled to the deformable outer membrane 604, the outer heat exchanger 1604 having an outer surface 1626 exposed to an external environment 601, and an inner surface 1628 exposed to the outer cavity 616. A thermoelectric generator 1606 may be positioned within the inner cavity 620, the thermoelectric generator 1606 comprising an outer surface 1630 exposed to the outer cavity 1620 through the deformable inner membrane 610. The thermoelectric generator 1606 may further have an inner surface 1632 that is thermally-coupled to an inner heat exchanger 1608. The energy harvesting device 1600 may further comprise a phase-change material membrane 628, at least a portion of the phase-change material membrane 628 coupled to the inner heat exchanger 1608, and encapsulating a mass of phase-change material 630.

The insulated container 1602 may comprise an outer membrane 604 that is impermeable. Further, and in contrast to the insulated container 1402, as schematically depicted in FIG. 14A and FIG. 14B, the insulated container 1602 may not be embodied with an aperture through the outer membrane 604. As such, an outer cavity 616 may be sealed. In one example, the outer cavity 616 may contain a mass of fluid 1620. As such, fluid 1620 may comprise, among others, air, nitrogen, or oxygen. In another implementation, the outer cavity 616 may be partially or wholly filled with an insulating material, such as a foam. As such, the foam may include one or more open-cell or closed-cell foams as described herein, or any other insulating foam known in the art. In another implementation, the outer cavity 616 may comprise a vacuum cavity.

In one example, the energy harvesting device 1600 may be configured to be transitioned between an expanded configuration, as schematically depicted in FIG. 16A, and a compressed configuration, as schematically depicted in FIG. 16B. In the expanded configuration of FIG. 16A, a separation distance 1622 may exist between an inner surface 1628 of the outer heat exchanger 1604, and an outer surface 1630 of the thermoelectric generator 1606. This separation distance 1622 may result in a comparatively higher thermal resistance along axis 1624, thereby reducing conduction through, and electrical energy produced by, the thermoelectric generator 1606. In comparison, when transitioned into a compressed configuration by force 1612, as schematically depicted in FIG. 16B, the outer heat exchanger 1604 may be urged towards the thermoelectric generator 1606. In this way, the separation distance 1622 may be reduced to approximately zero in the compressed configuration of FIG. 16B. As such, a thermal resistance substantially along axis 1624 may be comparatively lower in the compressed configuration than in the expanded configuration depicted in FIG. 16A.

FIG. 17A and FIG. 17B schematically depict another implementation of an energy harvesting device 1700, according to one or more aspects described herein. It is noted that energy harvesting device 1700 may include one or more elements similar to one or more elements described in relation to energy harvesting devices 600, 700, 800, 900, 1000, 1100, 1200, 1300, 1400, 1500, and 1600, (and/or any other energy harvesting device disclosed herein) where similar reference numerals represent similar components and features.

The energy harvesting device 1700 may comprise an insulated container 1702 that has an outer membrane 1714 encapsulating an internal cavity 1716. An outer heat exchanger 1704 may extend through the outer membrane 1714, such that the outer heat exchanger 1704 has an outer surface 1720 in contact with an external environment 601. In this way, the outer heat exchanger 1704 may be similar to the outer heat exchanger 624. A thermoelectric generator 1706 may be positioned within the internal cavity 1716, and sandwiched between the outer heat exchanger 1704, and an inner heat exchanger 1708. In one example, the thermoelectric generator 1706 may be similar to thermoelectric generator 622, and the inner heat exchanger 1708 may be similar to inner heat exchanger 626. An expandable membrane 1712 may encapsulate a mass of phase-change material 1710, such that at least a portion of the expandable membrane 1712 is coupled to the inner heat exchanger 7008. As such, the expandable membrane 1712 may be similar to expandable membrane 628, and the mass of phase-change material 1710 may be similar to phase-change material 630. Bi-directional conduction of heat between the phase-change material 1710, and the external environment 601 may be substantially along axis 1722 through the inner heat exchanger 1708, the thermoelectric generator 1706, and the outer heat exchanger 1704.

The internal cavity 1716 may be partially or wholly filled with a mass of air, nitrogen, oxygen, or another gas. Additionally or alternatively, the internal cavity 1716 may be partially or wholly filled with another fluid, or with a solid material. In one example, the internal cavity 1716 may be partially or wholly filled with an insulating foam, such as one or more of the foams described herein, or any other insulating foam known in the art. As the phase-change material 1710 absorbs heat energy from the external environment 601, the expandable membrane 1712 may deform to accommodate thermal expansion of the phase-change material 1710. As such, the expandable membrane 1712 may expand into the cavity 1716, and displace a material within the cavity 1716. The expandable membrane 1712 is shown in a comparatively expanded configuration in FIG. 17B. In one example, the cavity 1716 may comprise a vacuum. As such, where the term "vacuum" is used in this disclosure, it may be interpreted as a pressure (absolute pressure) below 1 atm. In another example, the term "vacuum" may refer to a pressure below 1 bar.

Figure 18:
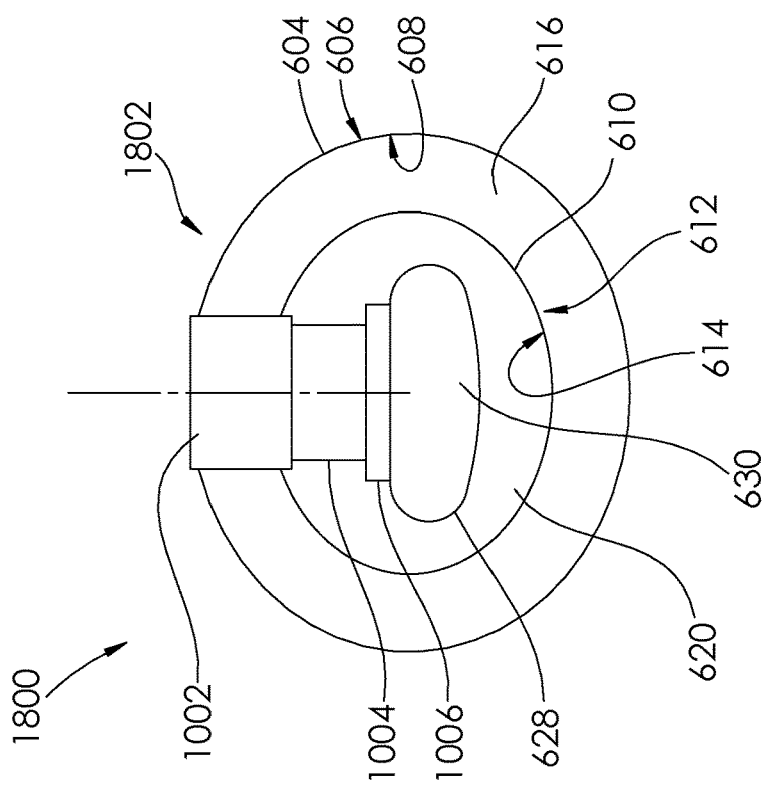
FIG. 18 schematically depicts another implementation of an energy harvesting device, according to one or more aspects described herein.

FIG. 18 schematically depicts another implementation of an energy harvesting device 1800, according to one or more aspects described herein. It is noted that energy harvesting device 1800 may include one or more elements similar to one or more elements described in relation to energy harvesting devices 600, 700, 800, 900, 1000, 1100, 1200, 1300, 1400, 1500, 1600, and 1700, where similar reference numerals represent similar components and features. Accordingly, energy harvesting device 1800 may be similar to energy harvesting device 1000, and have an insulated container 1802. In one example, the insulated container 1802 is not embodied with an opening. As such, the outer cavity 1616 may be sealed. As such, the outer cavity 1616 may be partially or wholly filled with a mass of fluid (air, nitrogen, oxygen, among others), and/or another insulating material, such as a polymeric foam.

Figure 19:
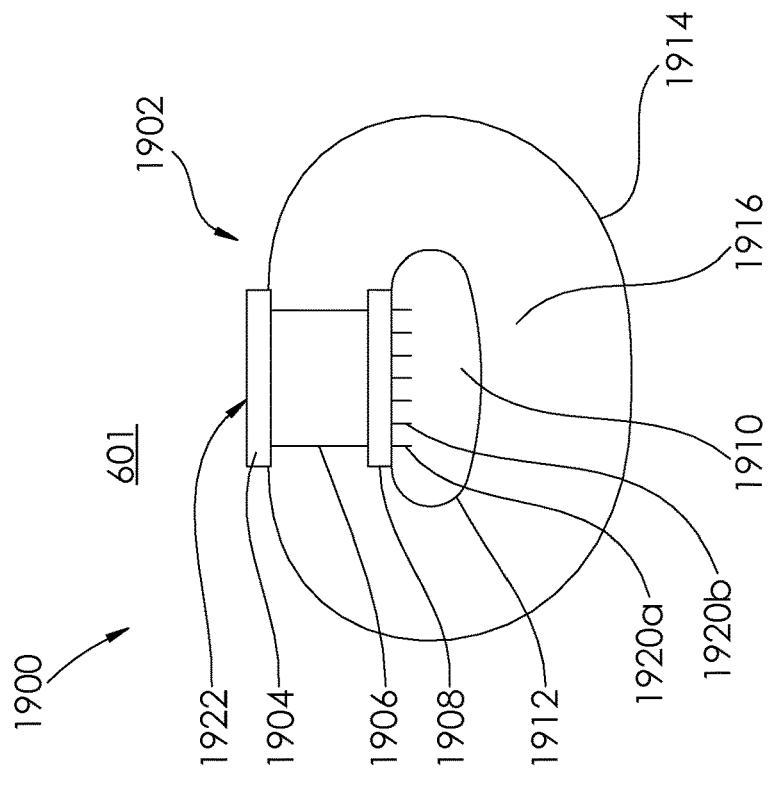
FIG. 19 schematically depicts another implementation of an energy harvesting device, according to one or more aspects described herein, in which the energy harvesting device is configured with an inner heat exchanger having one or more fins.

FIG. 19 schematically depicts another implementation of an energy harvesting device 1900, according to one or more aspects described herein. It is noted that energy harvesting device 1900 may include one or more elements similar to one or more elements described in relation to energy harvesting devices 600, 700, 800, 900, 1000, 1100, 1200, 1300, 1400, 1500, 1600, 1700, and 1800 (and/or any other energy harvesting device disclosed herein) where similar reference numerals represent similar components and features. In one example, the energy harvesting device 1900 may be similar to energy harvesting device 1700. As such, the energy harvesting device 1900 may comprise an insulated container 1902 that has an outer membrane 1914 encapsulating an internal cavity 1916. An outer heat exchanger 1904 may extend through the outer membrane 1914, such that the outer heat exchanger 1904 has an outer surface 1922 in contact with an external environment 601. In this way, the outer heat exchanger 1904 may be similar to the outer heat exchanger 624. A thermoelectric generator 1906 may be positioned within the internal cavity 1916, and sandwiched between the outer heat exchanger 1904, and an inner heat exchanger 1908. In one example, the thermoelectric generator 1906 may be similar to the thermoelectric generator 622. The inner heat exchanger 1908 may further comprise one or more fins, such as fins 1920a and 1920b. As such, the fins 1920a and 1920b may be configured to increase a surface area of the inner heat exchanger 1908, and thereby increase heat transfer between the thermoelectric generator 1906, and a material in contact with the inner heat exchanger 1908. The fins 1920a and 1920b may extend into an expandable membrane 1912 coupled to the inner heat exchanger 1908, such that the fins 1920a and 1920b may increase a surface area in contact with a phase-change material 1910. It will be appreciated that fins 1920a and 1920b may be embodied with different geometries in order to increase the efficacy with which heat is transferred between the inner heat exchanger 1908, and the phase-change material 1910. As such, those fins 1920a and 1920b are schematically depicted in FIG. 19, and a different number of fins, or different fin geometries, may be utilized with the energy harvesting device 1900, without departing from these disclosures. In another implementation, the outer heat exchanger 1922 may comprise one or more fins (not depicted).

FIG. 20 schematically depicts another implementation of an energy harvesting device 2000, according to one or more aspects described herein. It is noted that energy harvesting device 2000 may include one or more elements similar to one or more elements described in relation to energy harvesting devices 600, 700, 800, 900, 1000, 1100, 1200, 1300, 1400, 1500, 1600, 1700, 1800, and 1900, (and/or any other energy harvesting device disclosed herein) where similar reference numerals represent similar components and features. The energy harvesting device 2000 may comprise an insulated container 2002 that has an outer membrane 2016 encapsulating an internal cavity 2018. An outer heat exchanger 2004 may extend through the outer membrane 2016, such that the outer heat exchanger 2004 has an outer surface 2020 in contact with the external environment 601. In this way, the outer heat exchanger 2004 may be similar to the outer heat exchanger 624. A thermoelectric generator 2006 may be positioned within the internal cavity 2018, and thermally-coupled to the outer heat exchanger 2004 at a first side, and to a heat pipe 2008 at a second side. As such, those of ordinary skill in the art will recognize different implementations of the heat pipes 2008 that may be utilized to transfer heat between one or more elements of the energy harvesting device 2000, such as between the thermoelectric generator 2006, and an inner heat exchanger 2010. In one example, an expandable membrane 2014 may be coupled to the inner heat exchanger 2010, and encapsulate a mass of phase-change material 2012, similar to phase-change material 630.

FIG. 21 schematically depicts another implementation of an energy harvesting device 2100, according to one or more aspects described herein. It is noted that energy harvesting device 2100 may include one or more elements similar to one or more elements described in relation to energy harvesting devices 600, 700, 800, 900, 1000, 1100, 1200, 1300, 1400, 1500, 1600, 1700, 1800, 1900, 2000, (and/or any other energy harvesting device disclosed herein) where similar reference numerals represent similar components and features. Accordingly, the energy harvesting device 2100 represents one implementation of a device comprising multiple thermoelectric generators, such as thermoelectric generators 2106, and 2116. In particular, the energy harvesting device 2100 may comprise an insulated container 2102 having an outer membrane 2122 encapsulating a cavity 2120. An expandable membrane 2112 may be positioned within the cavity 2120, and encapsulate a mass of phase-change material 2110. Heat energy may be stored within the phase-change material 2110, and configured to be conducted in to/out from the phase-change material 2110 substantially along multiple axes, including axis 2130, and axis 2132. As such, heat energy may be conducted to/from the phase-change material 2110 through a first outer heat exchanger 2130, a first thermoelectric generator 2106, and a first inner heat exchanger 2108, and simultaneously conducted through a second outer heat exchanger 2118, a second thermoelectric generator 2116, and a second inner heat exchanger 2114. In one example, axes 2130 in 2132 may be parallel or substantially parallel to one another such that angle 2134 is proximate equal to 180° (or in another embodiments within 175-185 degrees). However, in another implementation, axes 2130 and 2132 may not be aligned with one another, and such that angle 2134 may be embodied with any angle value in the range of 0 to 360°, without departing from the scope of these disclosures. Further, an energy harvesting device, similar to energy harvesting device 2100, may be embodied with additional thermoelectric generators beyond those two generators 2106 and 2116 described in relation to FIG. 21.

Figure 22:
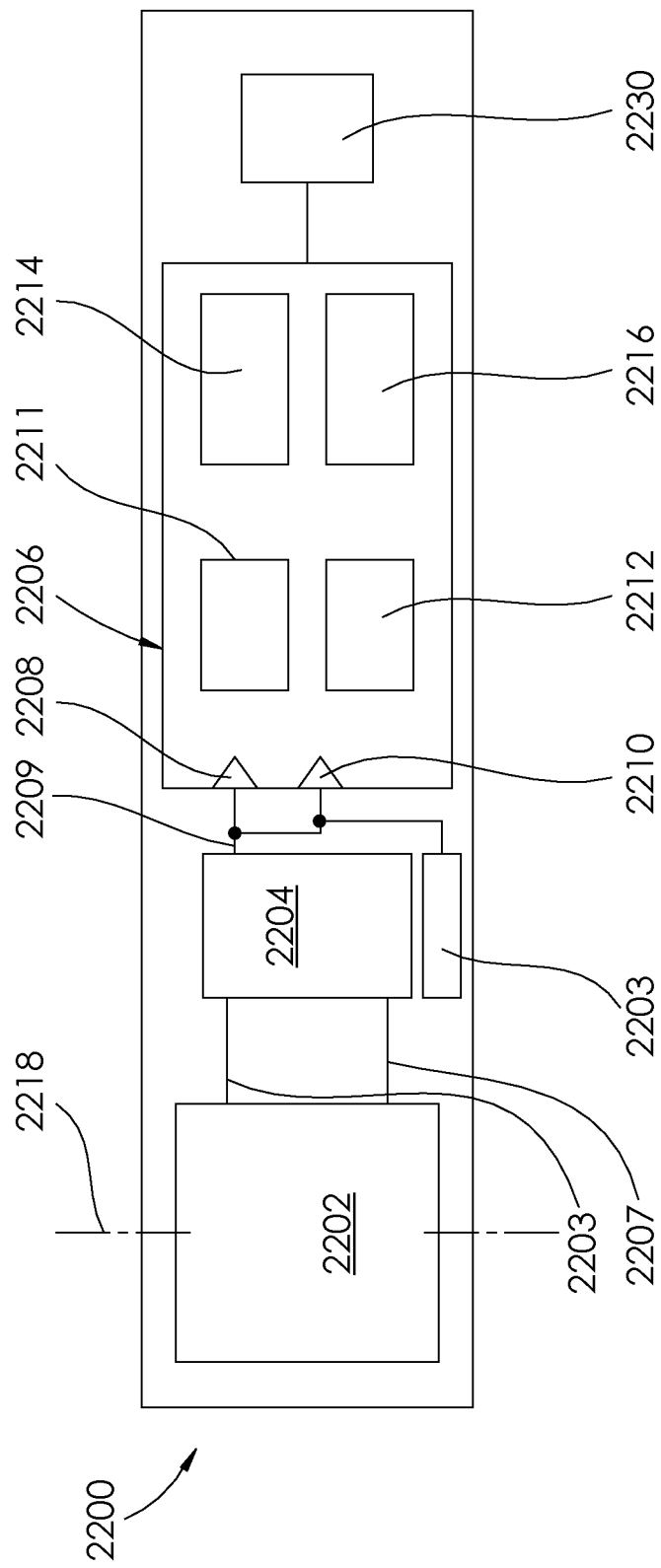
FIG. 22 schematically depicts a thermoelectric generator module, according to one or more aspects described herein.

FIG. 22 schematically depicts a thermoelectric generator module 2200, according to one or more aspects described herein. In one implementation, the thermoelectric generator module 2200 may comprise a thermoelectric generator 2202, in addition to multiple elements powered by the thermoelectric generator 2202, which will be described in further detail in the disclosure that follows. However, where a thermoelectric generator is described in this disclosure, such as thermoelectric generators 622, 1004, 1204, 1320, 1406, 1506, 1606, 1706, 1906, 2006, 2106, and/or 2116 (and/or any other thermoelectric generator disclosed herein), it may refer to a thermoelectric generator element in isolation, configured to generate electrical energy in response to an applied thermal gradient, or may refer to a thermoelectric generator module, such as module 2200, which includes elements in addition to the thermoelectric generator itself.

In one implementation, the thermoelectric generator module 2200 may comprise a thermoelectric generator 2202 that is configured to generate an electrical output in response to an applied thermal gradient. In one example, at least a portion of the thermoelectric generator module 2200 may be configured to facilitate heat conduction. For example, heat may be conducted substantially along axis 2218. Outputs 2205 and 2207 may be electrical channels (one or more circuit portions on a circuit board, or wires, among others) across which a voltage may be generated by the thermoelectric generator 2202. Accordingly, the polarities (positive and negative voltage) of the outputs 2205 and 2207 may switch in response to the direction of heat conduction substantially along axis 2218 (in response to a change in the side of the thermoelectric generator 2202 at a higher temperature). For example, when the phase-change material 630 is absorbing heat energy, an output from the thermoelectric generator 622 may have a first voltage polarity. However, when the phase-change material 630 is dissipating heat through the thermoelectric generator 622, an output from the thermoelectric generator 622 may have a second voltage polarity, opposite the first voltage polarity.

Accordingly, in one example, the thermoelectric generator module 2200 may include a rectifier module 2204 (otherwise referred to as a rectifier circuit 2204), configured to condition an output from the thermoelectric generator 2202. As such, the rectifier module 2204 may output a same voltage polarity at the output 2209 regardless of the direction of conduction of heat through the thermoelectric generator 2202. Those of ordinary skill in the art will recognize specific circuit elements, which may include one or more diodes, and which may be utilized to provide the functionality of the rectifier module 2204, without departing from the scope of this disclosure.

In one example, the output 2209 from the rectifier module 2204 may be fed into a battery module 2203. As such, the battery module 2203 may comprise one or more chemical cells, and may be utilized to store electrical energy generated by the thermoelectric generator 2202. The battery module 2203 may be configured to store any amount of energy, without departing from the scope of this disclosure. Additionally or alternatively, the output 2209 may be fed into one or more of an interrupt input 2208, and a power input 2210 of an activity monitoring circuit 2206. In one example, the interrupt input 2208 may monitor a voltage level, and execute an interrupt process in response to a voltage level (from output 2209) rising above a threshold interrupt voltage level. As such, the interrupt input 2208 may be utilized to transition, or "wake" the activity monitoring circuit 2206 from one or more states, including for example, a first power configuration to a second power configuration.

In one implementation, the activity monitoring circuit 2206 may be configured to generate sensor data and calculate one or more athletic measurements, which may comprise, among others, metrics related to a user's athletic performance. Accordingly, the activity monitoring circuit 2206 may comprise functionality similar to one or more of devices 128 or 400, among others.

In one example, a first power configuration of the activity monitoring circuit 2206 may correspond to a low-power configuration, and a second power configuration may correspond to a high power configuration. As such, a low-power configuration may further correspond to providing a comparatively low amount of electrical energy to one or more circuit elements of the activity monitoring circuit 2206. In turn, the high power configuration may comprise executing one or more processes to provide electrical energy to one or more additional circuit elements of the activity monitoring circuit 2206 than those provided with electrical energy in the low-power configuration. Additionally or alternatively, a high power configuration may provide an increased amount of electrical energy to one or more components of the activity monitoring circuit 2206. In another example, a first power configuration may provide approximately zero electrical energy to the activity monitoring circuit 2206, and a second power configuration may provide electrical energy to one or more circuit elements of the activity monitoring circuit. In another implementation, there may be multiple power distribution settings between a low power configuration and a high power configuration. As such, in one example, a voltage or a current output from the thermoelectric generator 2202 (or the rectifier element 2204) may be adjusted to a plurality of different levels between a first power configuration and a second power configuration. In another example, a first power configuration may correspond to one or more sensor elements (e.g. sensor 2212) being deactivated. Accordingly, in one example, when in a deactivated configuration, the one or more sensor elements may consume approximately no electrical energy. In turn, a second power configuration may correspond to one or more sensor elements (e.g. sensor 2212) operating in an active configuration, or the activity monitoring device being transitioned into an active state. In another example, there may be multiple power states, which in certain embodiments are based (at least partially) on an input signal from a monitoring circuit, such as activity monitoring circuit 2006. In one example, the power input 2210 may be configured to receive an electrical current from the rectifier circuit 2204 and distribute the received electrical energy to one or more of the central processing unit 2211, sensor 2212, memory 2214, and/or transceiver 2216, among other components.

The activity monitoring circuit 2206 of the thermoelectric generator module 2200 may be utilized to monitor physical activity undertaken by a user. As such, the activity monitoring circuit 2206, and as such, the thermoelectric generator module 2200, may be worn by a user, and include a sensor 2212 configured to output data in response to one or more motions of the user. As such, the sensor 2212 may include, among others, an accelerometer, a gyroscope sensor, a location-determining sensor, a force sensor, and/or any other sensor disclosed herein or known in the art. In one example, the activity monitoring circuit 2206 may be similar to one or more devices described in this disclosure, such as sensor device 128, among others. In one example, the memory 2214 (which may be a local non-transitory computer-readable medium) may store computer-executable instructions to be executed by the central processing unit 2211 (otherwise referred to as the processor 2211). In one implementation, the transceiver 2216 may be configured to communicate one or more portions of raw sensor data, or processed activity data determined from an output of the sensor 2212, to a remote device. In one implementation, activity data determined by the activity monitoring circuit 2206 may be communicated to a user interface 2230. As such, the user interface 2230 may include one or more of a display, one or more output indicator lights, a speaker, or a haptic feedback device, or combinations thereof.

Figure 23:
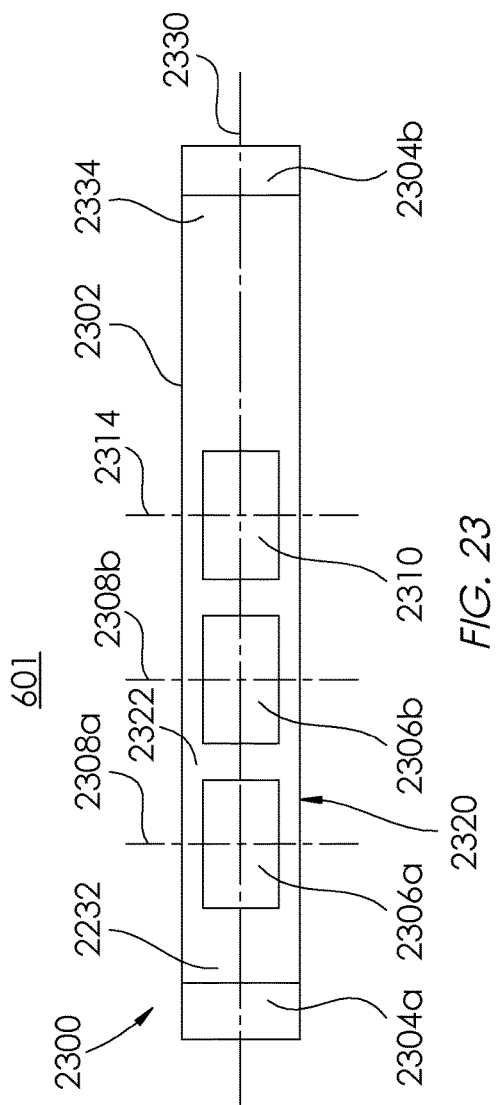
FIG. 23 schematically depicts a top view of an example of an activity monitoring device that may utilize one or more thermoelectric generators, according to one or more aspects described herein.

FIG. 23 schematically depicts a top view of an example of an activity monitoring device 2300 that may utilize one or more thermoelectric generators, according to one or more aspects described herein. In one example, the activity monitoring device 2300 may be utilized to detect one or more user motions associated with an activity being participated in by a user. In this way, the activity monitoring device 2300 may comprise one or more sensors, including, among others, accelerometer, a gyroscope sensor, a location determining sensor, and/or any other sensor disclosed herein or known in the art. In one example, the activity monitoring device 2300 may be similar to one or more elements previously described in this disclosure, such as, among others, sensor device 128.

In one example, the activity monitoring device 2300 may be configured to be worn on an appendage of the user. In one implementation, the activity monitoring device 2300 may be positioned proximate to a user's appendage when the device 2300 is worn. In one implementation, the activity monitoring device 2300 may comprise a flexible support structure 2302. In another example, the activity monitoring device 2300 may comprise a plurality of flexible support structures, similar to flexible support structure 2302, hingedly-connected, or flexibly-connected to one another along axis 2330. In another implementation, the activity monitoring device 2300 may comprise two or more rigid support structures hingedly-coupled to one another along axis 2330 in order to form a larger, flexible support structure, such as structure 2302. As such, the flexible support structure 2302 may comprise one or more woven or molded portions configured to allow the structure 2302 to be wrapped around an appendage of the user. In one example, the flexible support structure 2302 may comprise a first end 2332 that is spaced apart from a second end 2334 along a longitudinal axis 2330. The flexible support structure 2302 may have a first side 2322 that may be configured to be exposed to an external environment 601. Further, the flexible support structure 2302 may have a second side 2320, opposite the first side 2322, configured to be positioned proximate an area of skin of a user. In one example, the first end 2332 of the flexible support structure 2302 may comprise a first coupling mechanism 2304a. The second end 2334 of the flexible support structure 2302 may comprise a second coupling mechanism 2304b. As such, the first coupling mechanism 2304a may be configured to interface with the second coupling mechanism 2304b. As such, the combined coupling mechanism, comprising elements 2304a and 2304b, may include a clasp, a buckle, an interference fitting, a hook and loop fastener, and/or any other coupling mechanism disclosed herein or known in the art.

In one implementation, the activity monitoring device 2300 may include multiple thermoelectric generators, such as thermoelectric generators 2306a and 2306b. In one example, the thermoelectric generators 2306a and 2306b may include one or more elements of those thermoelectric generators 622, 1004, 1204, 1320, 1406, 1506, 1606, 1706, 1906, 2006, 2106, and/or 2116 previously described in this disclosure. In one example, the thermoelectric generators 2306a and 2306b may be connected in series, such that a voltage output from each of the generators 2306a and 2306b may add together. In another example, the thermoelectric generators 2306a and 2306b may be connected in parallel, such that a current output from each of the generators 2306a and 2306b may add together. The thermoelectric generators 2306a and 2306b may generate electrical energy in response to a thermal gradient applied substantially along axes 2308a and 2308b between the first side 2322 and the second side 2320. In one implementation, a first thermoelectric generator 2306a may be coupled to a first sub-portion of the flexible support structure 2302, and a second thermoelectric generator 2306b sub-portion of the flexible support structure 2302.

In one example, the activity monitoring device 2300 may include a thermoelectric generator module 2310, which may be similar to the thermoelectric generator module 2200 from FIG. 22. As such, the thermoelectric generator module 2310 may also be connected in series with the thermoelectric generators 2306a and 2306b, and generate electrical energy in response to a thermal conduction substantially along axis 2314. In one implementation, the activity monitoring device 2300, and in particular, the thermoelectric generator module 2310, may utilize one or more capacitors, batteries (similar to battery 2203), or a mass of phase-change material (similar to phase-change material 630), to store electrical energy. In another example, the activity monitoring device 2300 may not include an energy storage element.

Figure 24:
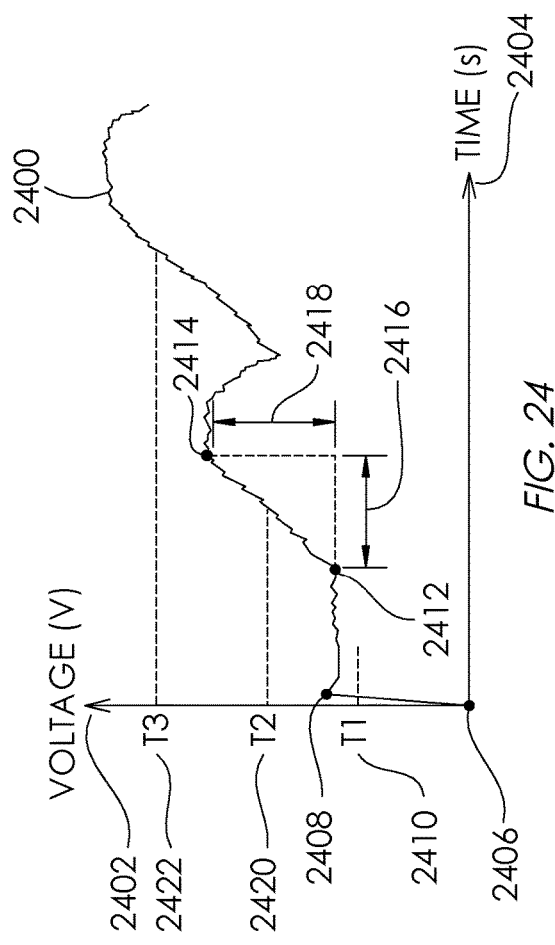
FIG. 24 schematically depicts an example graph of an output voltage from a thermoelectric generator, in accordance with various implementations.

FIG. 24 schematically depicts an example graph 2400 of an output voltage from a thermoelectric generator in accordance with various implementations. In one example, graph 2400 may represent an output voltage from a thermoelectric generator, such as thermoelectric generator 622, which is generating electrical energy in response to a temperature gradient between an external environment and a user's skin temperature (user's body temperature). As such, the thermoelectric generator associated with graph 2400 may not utilize an energy storage medium, such as a phase-change material 630. Accordingly, point 2406 may correspond to a time at which the thermoelectric generator is brought into contact with a user's body. As such, the thermoelectric generator, at point 2406 may transition from a thermal equilibrium (no temperature gradient across the thermoelectric generator) to having a temperature gradient corresponding to a temperature difference between a skin temperature of the user, and an environmental temperature (e.g. room temperature, mean outdoor air temperature). As such, a voltage output from the thermoelectric generator may increase to point 2408. In one example, one or more sensor components, such as those elements described in relation to the thermoelectric generator module 2200, may detect the voltage increase between points 2406 and 2408 and determine that a device containing the thermoelectric generator has been put on/is now in use by the user. In one example, when the voltage increases above a first threshold 2410, one or more detection circuits may determine that the user is now wearing the thermoelectric generator.

As a user exercises, the user's skin temperature may increase. Consequently, a thermal gradient across the thermoelectric generator may also increase and/or increased perspiration may be absorbed or in contact with one or more elements of the device. The period between points 2412 and 2414, delimiting an output voltage increase, may correspond to a period of increased activity by the user (e.g. the user may be exercising at a moderate exertion level). Accordingly, one or more detection circuits, such as one or more elements of the thermoelectric generator module 2200, may be utilized to detect a second threshold 2420 corresponding to this period of increased activity and/or a slope of the output voltage corresponding to the change in voltage 2418 divided by the change in time 2416. Similarly, a third threshold output voltage 2422 may be detected, such as by the thermoelectric generator module 2200, and may be determined as corresponding to a period of increased activity (e.g. the user may be exercising as a severe exertion level, among others). Thus, embodiments may utilize detected outputs from the device, such as voltage, to detect activity levels. In this regard, certain embodiments may be utilized to classify the user's activity. For example, it has been discovered by the inventors that voltage output levels may be used to detect when the user is inactive, sitting, standing, walking, or running. As such, in one example, an output voltage increasing above a threshold voltage may identify a user as transitioning from walking to running, among others. Other categorizations are within the scope of this disclosure. In this regard, certain embodiments, may utilize voltage readings in combination with other inputs (such as from one or more sensors) to determine activity levels, energy expenditure, activity classification, among other attributes. Further embodiments may utilize battery levels, voltage output rate or thresholds, and/or factors to increase sampling rate of the activity measurement processes. For example, a voltage level above a first threshold may sample activity measurements at a first sampling rate and a voltage level above a second threshold may result in a second sampling rate that is higher than the first sampling rate. In other embodiments, different sensors may be activated (or activated at a quicker interval) based upon voltage levels and/or other inputs.

In one implementation, a voltage output from a thermoelectric generator, such as thermoelectric generator 2202, may be monitored by a processor, such as processor 2211. Accordingly, a voltage output from the thermoelectric generator 2202 may be proportional to heat flux across the thermoelectric generator 2202 (i.e. along axis 2218). As such, the thermoelectric generator 2202 may be utilized as a heat flux sensor, and such that a voltage detected by the processor 2211 may be mapped to a heat flux across the thermoelectric generator 2202. In one implementation, an output from a thermoelectric generator, such as thermoelectric generator 2202, may be utilized to estimate a remaining amount of heat energy stored within a phase-change material, such as within the phase-change material 630 stored within the expandable membrane 628.

Figure 25:
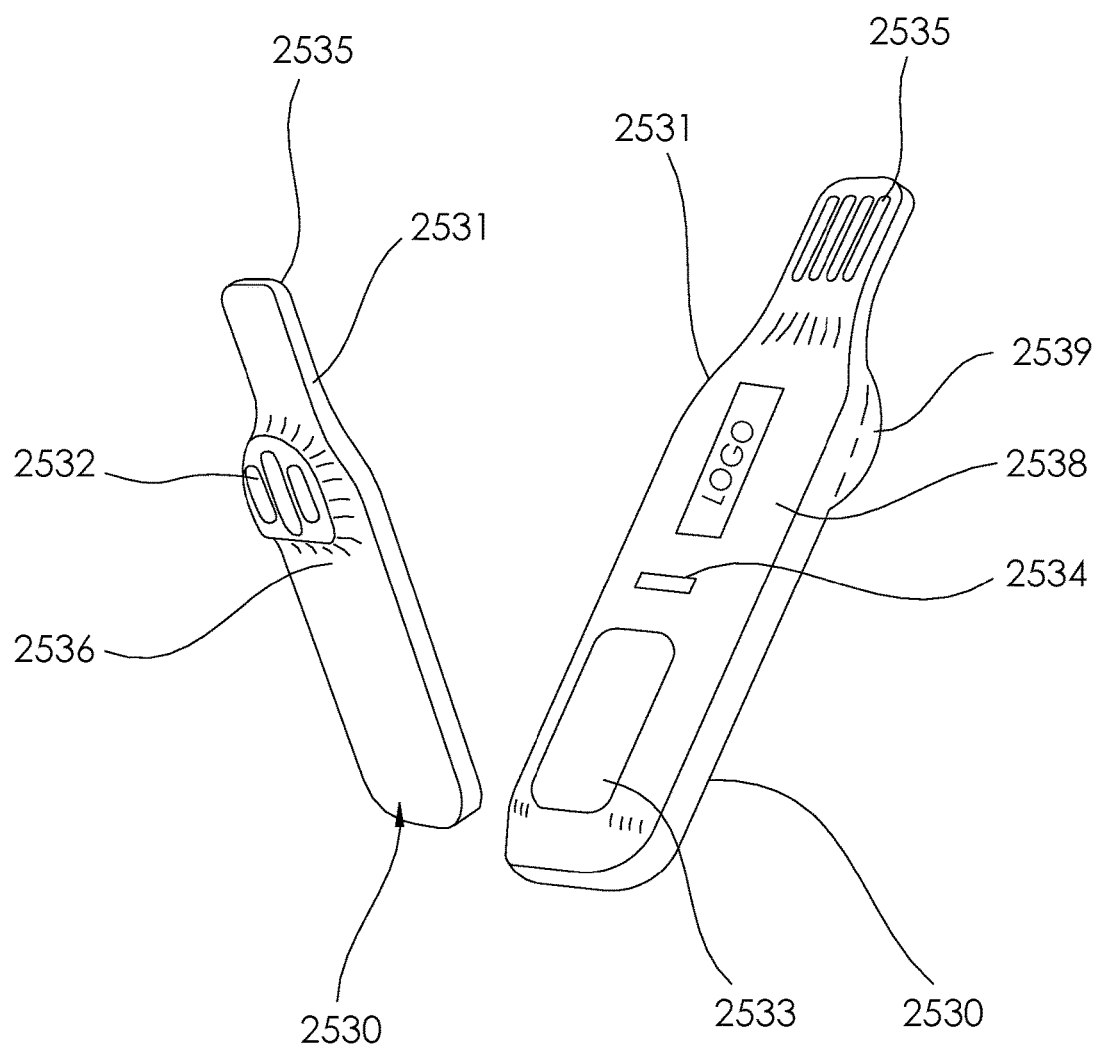
FIG. 25 depicts an example module that may be used in association with apparel or other devices, such as being insertable within an armband, clothing, wearable device, handheld device, textile, and/or an apparatus that may be used during physical activity.

Certain aspects relate to energy harvesting devices that may include or be utilized in conjunction with a module. FIG. 25 shows an example module 2530 that may be used in association with apparel or other devices, such as being insertable within an armband, clothing, wearable device, handheld device, textile, and/or an apparatus that may be used during physical activity. Module 2530 may include one or more mechanical, electric, and/or electro-mechanical components, such as computer components, that are described elsewhere herein, as well as a casing 2531 forming a structural configuration for the module 2530. Module 2530 may comprise at least one of a processor, a non-transitory computer-readable medium, sensor and/or a transceiver. One or more components may be similar to and/or identical to any component shown and described above in FIGS. 1-5. Those skilled in the art will appreciate that module 2530 and the casing 2531 may have multiple different structural configurations and the illustrations are merely exemplary.

In the embodiment of FIG. 25, the module 2530 has at least one sensor 2532, which may be in the form of, for example, a heart rate sensor. Module 2530 may be configured to contact the skin of the user during wear while the module 2530 is secured within a band, device or apparatus, etc. For example, the heart rate sensor 2532 in this illustrated embodiment may be an optical sensor that works best in contact or close proximity with the skin. As shown in FIG. 25, the casing 2531 of module 2530 has a projection 2539 on the underside 2536, and the sensor 2532 is mounted on the end of the projection 2539. The projection 2539 extends the sensor 2532 farther away from the surrounding surfaces of the casing 2531, permitting greater capability for forming continuous contact with the user's body. Band 2520 may have an aperture that allows a front surface of the protrusion to contact the user's skin, however, the remainder of underside 2538 is held within the band 2520 or at least is separated from the user's skin by at least one layer of a material. In one embodiment, the layer of material may be configured to wick away moisture (e.g., such as sweat) away from the sensing surface on the user's skin.

In one embodiment, a layer of material may be configured to collect or wick moisture of fluid towards a heat transfer plate of other component of the device.

In other embodiments, it may be configured to prevent moisture, light, and/or physical materials from contacting the sensing surface or location during the physical activity. In one embodiment, it may selectively block light of certain wavelengths. In certain embodiments, at least 95% of ambient light is blocked within the immediate vicinity of the sensing surface. In another embodiment, at least 99% of the ambient light is blocked. This may be advantageous for optical sensors, such as optical heart rate sensors. Those skilled in the art will appreciate that other sensors, including those sensors described above in relation to FIGS. 1-5, may be used—either alone in combination with each other or other sensors—without departing from the scope of this disclosure.

In one general embodiment, the module 2530 may include one or more user input interfaces, such as for example, buttons 2533 to provide user-actuated input. An example user input interface may consist of single mechanical button, e.g., button 2533, which is shown on the top side 2537 opposite the underside 2536. Yet in other embodiments, display feature 2534 may be configured as a user-input interface. Those skilled in the art will appreciate that one or more user-actuated inputs may also be received through one or more transceivers of the module 2530. For example, a system may be configured such that a user may be able to enter a user input onto an electronic mobile device which may mimic using buttons 2533 or, alternatively, perform different functions than available in a specific instance of actuating buttons 2533. Module 2533 may further comprise one or more display features 2534.

In one embodiment, the pocket 2540 of the band or apparatus may be configured to receive module 2530 having a display feature 2534 on surface that provides at least one visual indicia to a user. Display features 2534 may be a simple light source, such as a light emitting diode. In a specific embodiment, the color, intensity, or pattern of illumination of at least one light source in display features may be used to provide a visual indication to the user. Those skilled in the art will further appreciate that more complex display devices, such as LED, OLED, LCD, etc. may be utilized. Other output mechanisms, such as audible and tactile are within the scope of this disclosure.

Module 2530 may further include one or more connectors 2535 for charging and/or connection to an external device. In one embodiment, connectors 2535 may include a serial bus connection, such as that may comply with one or more Universal Serial Bus (USB) standards. In one embodiment, connectors 2535 may be configured to provide at least of the same electronic information to an external device that may be transmitted via one or more transceivers of the module 2530.

When the module 2530 in the embodiment of FIG. 25 is received within a pocket or pouch, connector 2535 is received within the shell 2548, the underside 2536 of the casing 2531 is positioned in contact with the inner wall 2544 of the pocket 2540, and the top side 2537 of the casing 2531 is positioned in contact with the outer wall 2543 of the pocket 2540. In this arrangement, the projection 2539 extends through the sensor opening 2545 to place the sensor 2532 in closer proximity with the user's body, the button 2533 is positioned adjacent the button portion 2547 on the outer wall 2543, and the light 2534 is positioned in alignment with the window 2546 to permit viewing of the light 2534 through the outer wall 2543. The projection 2539 extending through the sensor opening 2545 and also in certain embodiments may assist in holding the module 2530 in place. In this configuration the end of the module 2530 opposite the connector 2535 protrudes slightly from the access opening 2542, in order to facilitate gripping for removal of the module 2530.

The casing 2531 may have a structural configuration to increase comfort of wearing the module 2530 in close proximity to the user's skin. For example, the casing 2531 has a flat configuration to create a thin profile, making the module 2530 less noticeable when being worn on the user's body. As another example, the casing 2531 may have curved contours on the underside 2536 and the top side 2537, as well as curved or beveled edges, in order to enhance comfort.

In certain embodiments, computer-executable instructions may be used to calibrate a device or system, such as to account for the location, orientation, or configuration of a sensor or group of sensors. As one example, module 2530 may include a heart rate sensor. The heart rate sensor may be configured such that when correctly orientated on or in the band, the heart rate sensor is located or oriented a certain way with respect to the user. For example, if the heart rate sensor is an optical heart rate sensor, it may be within a distance range to the skin (with respect to multiple axes and location). Further, one or more sensors may be configured such that when correctly oriented within the band (e.g., placed within the pocket), a contact of a sensor is configured to be in communication with the user (e.g., their skin or alternatively their clothing). Too much variance with respect to the orientation or location of the sensor may result in inaccurate and/or imprecise data. In certain embodiments, one or more sensor measurements, either raw or calculated, may be utilized to determine a proper or preferred orientation(s) or location(s) of the sensor(s).

The measurements may be based on one or more remote or local sensors on the device to be oriented, such as module 2530. For example, in certain embodiments, a user's Body Mass Index (BMI) or another parameter may be calculated. The calculation may be based, at least in part, on one or more sensors located on the device to be oriented. Based upon the sensor measurement(s), a UI, which may be on the device itself, a remote device, and/or a device in electronic communication with the device to be oriented (or re-oriented) may prompt and/or guide a user to re-orient the device. In other embodiments, it may provide a user input device to provide user inputs for orientation. For example, unlike prior art devices which may merely detect a weak or imprecise value and recommend or request the orientation of the sensor or device, embodiments disclosed herein may use data to intelligently determine the problem and/or solution. In one embodiment, a user's BMI or other data may be used to determine that the user should wear the device at another location and/or alter its orientation. For example, if a user's BMI is within the normal range (e.g., commonly accepted as 20-25), however, heart rate data is utilized in the calculation of a parameter that is below a threshold, then in certain embodiments, additional analysis may be performed to consider whether the heart rate sensor should be adjusted. As explained in more detail below, further embodiments relate to augmenting one or more calculations of parameters used in the calculations.

Systems and methods may be implemented to reduce inaccuracies and/or imprecise data collection. In one embodiment, the band may be configured to be worn within a range of locations, such as on a user's appendage or extremity. With respect to a "lower arm" usage example, the lower arm may be considered the distance between an elbow joint and the carpus of an arm or appendage, and may further be logically divided into a proximate region and a distal region. For example, the proximate region of the lower arm would include a portion (e.g., up to half) of the lower arm closest to the user's shoulder; and likewise, a distal region would include a portion (e.g., up to the remaining half) of the lower arm connecting to the carpus. In this regard, a band may be configured to be worn in the proximate region of the lower arm. In one embodiment, the entire band is configured to be retained within a proximate half of the lower arm. In one embodiment, the band is configured to be retained at a specific location during athletic activities, such as with respect to the distance of the lower (or upper arm), a sensor measurement location is configured to move less than 1% or 0.5% of the distance along the lower arm. In yet other embodiments, the band may be configured to move within a specific distance with respect to the distance along the lower arm, however, at least one sensor (such as a sensor of the module 2530) may be configured to move a smaller distance. For example, in one embodiment, a band may be configured to permit movement of about 1 mm along the length of the lower arm, however, the module, or a sensing surface of the module, may be configured to only permit 0.55 mm movement along the same axis. As discussed above, one or more measurements may dictate altering this range, the distance from the sensor to the skin, as well as other locational dimensions and/or orientations. In one embodiment, a band may be configured to retain a sensing surface (or sensing location) of the module at least a predefined distance from the carpus. This may be due to the mechanical properties of a band, the module 2530, and/or as a result of a sensor providing an indication of an incorrect and/or correct usage of a band and/or module 2530. In yet another embodiment, the sensing surface is at least located 20% of the distance away from the carpus. In another embodiment, the band may be configured to retain a sensing surface of the band at least a predefined distance of the distance from the elbow joint (or equivalent).

In one embodiment, one or more sensors of the module (alone and/or with other external sensors) may be utilized to detect the location of the module 930, a sensing surface of the module, a sensing location, and/or a band. This may be done directly or indirectly. In certain embodiments, one or more non-transitory computer-readable mediums may comprise computer-executable instructions, then when executed by a processor cause the processor to at least conduct a location calibration routine. The computer-readable medium(s) may be located entirely on the module, an external electronic device, such as a mobile or cellular device, and/or combinations thereof. One or more calibration routines may be automatically initiated, such as by being triggered by sensing one or more criteria (e.g. with a sensor of the module) or through a manual initiation, such as by a user initiating the routine.

Movements during the athletic activity will naturally cause physical movements of anatomical structures, including joints and flexing muscles. As one example, flexing muscles may cause relative and absolute changes in locations and orientation of sensor sensing surfaces and/or sensing locations. As discussed herein, having the band, sensing surfaces, and/or sensing locations located in positions to reduce or eliminate flexure-causing inaccuracies will improve the utility of such sensing systems when compared with prior-art systems. For example, the device (or location(s)) may be positioned to reduce or eliminate forearm tension in one embodiment. In another embodiment, systems and methods may be implemented to identify the extent of actual and/or anticipated flexure or anatomical movement. In further embodiments, one or more calibration or correction factors may be applied to sensor readings based upon flexure or other anatomical movements. In one embodiment, only flexure of one muscle or group of muscles may be considered. This may be the case even when other muscles' flexure is present.

CONCLUSION

Aspects of the embodiments have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the embodiments.

For the avoidance of doubt, the present application extends to the subject-matter described in the following numbered paragraphs (referred to as "Para" or "Paras"):
1. An energy harvesting device comprising:
an insulated container, comprising:
a first membrane defining at least a portion of an inner cavity;
a thermoelectric generator operably coupled to the first membrane; and
an expandable membrane disposed within the first cavity and operably coupled to the thermoelectric generator, the expandable membrane encapsulating a mass of phase-change material configured to store heat energy.
2. An energy harvesting device according to Para 1, wherein the thermoelectric generator is coupled to the first membrane via a first heat exchanger.
3. An energy harvesting device according to Para 1 or 2, wherein the thermoelectric generator is coupled to the expandable membrane via a second heat exchanger.
4. An energy harvesting device according to Para 3, wherein the second heat exchanger comprises at least one fin in contact with the phase-change material.
5. An energy harvesting device according to Para 3 or 4, wherein the thermoelectric generator is coupled to the second heat exchanger via a heat pipe.
6. An energy harvesting device according to any of Paras 2 to 5, wherein the or each heat exchanger comprises an aluminum alloy.
7. An energy harvesting device according to any of the preceding Paras, wherein an insulating material is provided within the inner cavity so as to insulate the phase-change material.
8. An energy harvesting device according to Para 7, wherein the insulating material comprises a mass of gas.
9. An energy harvesting device according to Para 7 or 8, wherein the insulating material comprises a foam.
10. An energy harvesting device according to any of Paras 1 to 6, wherein the inner cavity comprises a vacuum.
11. An energy harvesting device according to any of the preceding Paras, wherein the first membrane is deformable.
12. An energy harvesting device according to any of the preceding Paras, further comprising a second membrane, wherein an outer cavity is formed between the first and second membranes.
13. An energy harvesting device according to Para 12, wherein an insulating material is provided within the outer cavity.
14. An energy harvesting device according to Para 13, wherein the insulating material comprises a mass of gas.
15. An energy harvesting device according to Para 13 or 14, wherein the insulating material comprises a foam.
16. An energy harvesting device according to Para 15, wherein the second membrane is permeable to allow water to soak into the foam.
17. An energy harvesting device according to Para 16, wherein the foam is configured to retain sufficient water to protect the thermoelectric generator and the expandable membrane from being exposed to a temperature of air in the external environment above a failure temperature.
18. An energy harvesting device according to Para 12, wherein the outer cavity comprises a vacuum.
19. An energy harvesting device according to any of Paras 11 to 16, wherein the second membrane forms an outer membrane having an surface in contact with the external environment, wherein the second membrane is provided with an aperture extending from the outer surface of the outer membrane to the inner surface of the outer membrane, the aperture configured to permit an ingress of air and/or water from the external environment into the outer cavity.
20. An energy harvesting device according to Para 19, wherein the aperture is configured to allow water to enter into the outer cavity during a wash cycle as the item of clothing is laundered, and
wherein the phase-change material is configured to store a portion of heat energy captured during a dryer cycle as the item of clothing is laundered.

21. An energy harvesting device according to Para 19 or 20, wherein the aperture is configured to release water vapor from the outer cavity.

22. An energy harvesting device according to any of Paras 19 to 21, wherein the aperture is substantially aligned with a primary axis of conduction of the insulated container.

23. An energy harvesting device according to any of Paras 12 to 22, wherein the second membrane is deformable.

24. An energy harvesting device according to Para 23, wherein the insulated container is configured to be deformed between an expanded configuration and a compressed configuration,
wherein, when in the expanded configuration, the thermoelectric generator is spaced from one of the first and second membranes, and, when in the compressed configuration, the thermoelectric generator is thermally coupled to said one of the first and second membranes to allow bi-directional conduction of heat between the phase-change material and the external environment.

25. An energy harvesting device according to Para 24, wherein, when in the expanded configuration, the thermoelectric generator is spaced from a heat exchanger disposed between the thermoelectric generator and said one of the first and second membranes.

26. An energy harvesting device according to Para 24 or 25, wherein the device has a comparatively high thermal resistance to heat conduction through the thermoelectric generator when in the expanded configuration and a comparatively low thermal resistance to heat conduction through the thermoelectric generator when in the compressed configuration.

27. An energy harvesting device according to any of Paras 24 to 26, wherein the insulated container is configured to be deformed from the expanded configuration to the compressed configuration when an item of clothing comprising the device is positioned on a user.

28. An energy harvesting device according to any of the preceding Paras, further comprising an activity monitoring circuit connected to the thermoelectric generator.

29. An energy harvesting device according to Para 28, wherein the activity monitoring circuit is configured to monitor a voltage output from the thermoelectric generator, and wherein the output voltage is proportional to an activity level of the user such that an activity is identifiable by the activity monitoring circuit based on output voltage.

30. An energy harvesting device according to Para 29, wherein the output voltage is proportional to a temperature gradient between a user's skin and an external environment.

31. An energy harvesting device according to Para 30, wherein the output voltage being above a threshold voltage indicates that the user is wearing the energy harvesting device.

32. An energy harvesting device according to Para 30 or 31, wherein the output voltage rising above a threshold voltage identifies the user as transitioning from walking to running.

33. An energy harvesting device according to any of Paras 28 to 32, wherein the activity monitoring circuit comprises a sensor.

34. An energy harvesting device according to Para 33, wherein the sensor comprises an accelerometer.

35. An energy harvesting device according to Para 33 or 34, wherein the sensor comprises a location-determining sensor.

36. An energy harvesting device according to any of Paras 28 to 35 when appended to any of Paras 24 to 27, wherein when transitioned from the expanded configuration to the compressed configuration, a voltage output generated by the thermoelectric generator transitions from a first voltage to a second voltage.

37. An energy harvesting device according to Para 36, wherein the change in voltage is indicative of an external force being applied to the insulated container of the energy harvesting device.

38. An energy harvesting device according to Para 36 or 37, wherein the transition in voltage output transitions the activity monitoring circuit from a first power configuration to a second power configuration.

39. An energy harvesting device according to Para 38, wherein the first power configuration is a low power configuration that provides a first amount of electrical energy to the activity monitoring circuit, and the second power configuration is a high power configuration that provides a second amount of electrical energy, higher than the first amount of electrical energy, to the activity monitoring circuit.

40. An energy harvesting device according to Para 39, wherein the first power configuration corresponds to the activity monitoring circuit being deactivated and the second power configuration corresponds to the activity monitoring circuit being activated.

41. An energy harvesting device according to any of Paras 28 to 40, wherein the activity monitoring circuit comprises a radio transmitter, and at least a portion of the insulated container is radio-wave transparent.

42. An energy harvesting device according to any of the preceding Paras, wherein the first membrane is impermeable.

43. An energy harvesting device according to any of the preceding Paras, wherein the insulated container is impermeable to water at 1 atm.

44. An energy harvesting device according to any of the preceding Paras, wherein the insulated container is configured to be positioned on or within an item of athletic apparel.

45. An energy harvesting device according to any of the preceding Paras, wherein the thermoelectric generator further comprises a rectifier circuit configured to output a voltage with a same (constant) polarity as heat energy is transferred into and out from the container structure.

46. An energy harvesting device according to any of the preceding Paras, wherein the phase-change material is configured to reach an approximate thermal equilibrium with the external environment at approximately 20 degrees Celsius within at least 4 hours.

47. An energy harvesting device according to any of the preceding Paras, wherein the phase-change material comprises a salt-hydrate material.

48. An energy harvesting device according to any of the preceding Paras, further comprising a processor powered by the thermoelectric generator, wherein the processor is configured to monitor a voltage output from the thermoelectric generator, and wherein the voltage output is proportional to a thermal gradient across the thermoelectric generator such that the thermoelectric generator functions as a heat flux sensor.

49. An energy harvesting device according to Para 48, wherein the voltage output is indicative of an amount of remaining heat energy stored with a phase-change material.

50. An energy harvesting device according to any of the preceding Paras, wherein the thermoelectric generator is configured to generate electrical energy based on a thermal gradient across the thermoelectric generator, and without an auxiliary energy storage medium.

51. A method of operating an energy harvesting device according to any of the preceding Paras, exposing the insulated container to an external environment having an elevated temperature which is higher than the temperature of the phase-change material such that the phase-change material stores a portion of heat energy captured.

52. A method according to Para 51, wherein the insulated container is exposed to the elevated temperature during a dryer cycle as an item of clothing comprising the insulated container is laundered.

53. A method according to Para 51 or 52, wherein the elevated temperature is in a range of approximately 45-85 degrees Celsius.

54. A method according to any of Paras 51 to 53, wherein the insulated container absorbs water during a wash cycle which evaporates during the dryer cycle, such that the thermoelectric generator and the expandable membrane are exposed to a temperature range below a failure temperature.

55. An activity monitoring device, comprising:
 a support structure comprising a first end spaced apart from a second end along a first axis, the support structure further comprising a first side configured to be exposed to an external environment, and a second side, opposite the first side along a second axis, the second side configured to be positioned proximate to an area of skin of the user;
 a processor;
 an activity monitoring circuit coupled to the support structure and configured to provide sensor data to the processor from which the processor can calculate athletic measurements based upon a user's athletic movements; and
 a thermoelectric generator module configured to generate and transfer electrical energy to the processor and the activity monitoring circuit,
 wherein the thermoelectric generator module is configured to generate electrical energy in response to a thermal gradient between the first side and the second side.

56. An activity monitoring device according to Para 55, wherein the device comprises at least two thermoelectric generator modules.

57. An activity monitoring device according to Para 55, wherein the thermoelectric generator modules are connected in series.

58. An activity monitoring device according to any of Paras 55 to 57, wherein the support structure is a first support structure, the device further comprising a second support structure flexibly coupled to the first support structure.

59. An activity monitoring device according to Para 58, wherein the first support structure comprises a first thermoelectric generator module and the second support structure comprises a second thermoelectric generator module.

60. An activity monitoring device according to Para 59, wherein each support structure comprises at least two thermoelectric generator modules.

61. An activity monitoring device according to Para 60, wherein the thermoelectric generator modules of each support structure are connected in series.

62. An activity monitoring device according to any of Paras 59 to 61, wherein the first support structure is connected to the second support structure along the first axis.

63. An activity monitoring device according to any of Paras 59 to 62, wherein the first support structure and the second support structure are each rigid structures.

64. An activity monitoring device according to any of Paras 55 to 63, wherein the activity monitoring circuit comprises an optical sensor configured to be fully powered by the thermoelectric generator(s), wherein the optical sensor is configured to be positioned proximate to a user's appendage when the device is worn.

64. An activity monitoring device according to any of Paras 55 to 63, wherein the activity monitoring circuit is a first activity monitoring circuit and the device further comprises a second activity monitoring circuit, wherein the second activity monitoring circuit comprises an optical sensor configured to be fully powered by the thermoelectric generator(s), wherein the optical sensor is configured to be positioned proximate to a user's appendage when the device is worn.

65. An activity monitoring device according to any of Paras 55 to 64, wherein the activity monitoring circuit comprises an accelerometer.

66. An activity monitoring device according to any of Paras 55 to 65, wherein the processor is configured to determine that the thermoelectric generator module(s) produced a threshold quantity of energy; and
 based upon the threshold quantity of energy being produced, altering capture of athletic measurements from the device.

67. An activity monitoring device according to Para 66, wherein the altering of the capture comprises reducing a sampling rate from at least one sensor.

68. An activity monitoring device according to Para 66 or 67, wherein the altering of the capture comprises ceasing capturing data from at least one sensor.

69. An activity monitoring device according to any of Paras 55 to 68, wherein the support structure is flexible and a first coupling mechanism is provided at the first end configured to be removably-coupled to a second coupling mechanism at the second end.

70. An activity monitoring device according to any of Paras 55 to 69, wherein the processor is configured to:
 determine that the sensor data is indicative of a threshold level of athletic movement, and in response, causing the device to enter into a first active state;
 based upon the sensor data obtained from the device while in the first active state, calculate athletic measurements based upon a user's athletic movements; and
 switch the device to a second active state, and based upon the sensor data from the device while in the second active state, calculating athletic measurements based upon the user's athletic movements.

71. An activity monitoring device according to any of Paras 55 to 70, wherein the support structure is flexible and comprises a plurality of individual rigid interconnected components, wherein at least a first and a second individual interconnected components of the plurality of components each comprise a first end spaced apart from a second end along a first axis.

72. An activity monitoring device according to any of Paras 55 to 71, further comprising a transceiver configured to automatically transmit the calculated athletic measurements to a mobile device.

What is claimed is:
1. An energy harvesting device, comprising:
 an insulated container, comprising:
  a deformable outer membrane having an outer surface and an inner surface;
  a deformable inner membrane, spaced apart from the deformable outer membrane, having an outer surface and an inner surface;
  an internal cavity spaced between the deformable outer membrane and the deformable inner membrane;
  an outer heat exchanger coupled to the deformable outer membrane, comprising an outer surface exposed to an external environment, and an inner surface exposed to the internal cavity;

an inner heat exchanger coupled to the deformable inner membrane, comprising an outer surface exposed to the external environment, and an inner surface;

a thermoelectric generator module positioned within the internal cavity, the thermoelectric generator coupled to the inner heat exchanger, and comprising an outer surface exposed to the internal cavity, the insulated container having a primary axis of conduction through the inner heat exchanger, the thermoelectric generator, and the outer heat exchanger; and a processor, wherein the insulated container is configured to be deformed between an expanded configuration and a compressed configuration, wherein when in the expanded configuration, the inner surface of the outer heat exchanger is spaced apart from the outer surface of the thermoelectric generator, wherein when in the compressed configuration, the inner surface of the outer heat exchanger is positioned proximate to the outer surface of the thermoelectric generator, wherein the processor is powered by the thermoelectric generator, wherein the processor is configured to monitor a voltage output from the thermoelectric generator, and wherein the output voltage is proportional to a thermal gradient between the outer and inner heat exchangers such that the thermoelectric generator functions as a heat flux sensor.

2. The energy harvesting device of claim 1, wherein the thermal gradient between the inner and outer heat exchangers is between a temperature of the external environment and a user's skin temperature.

3. The energy harvesting device of claim 1, wherein the output voltage being above a threshold voltage indicates that a user is wearing the energy harvesting device.

4. The energy harvesting device of claim 1, wherein the inner and outer heat exchangers comprise aluminum alloys.

5. The energy harvesting device of claim 1, wherein the insulated container comprises a closed-cell foam.

6. The energy harvesting device of claim 1, wherein the insulated container is impermeable to water at 1 atm.

7. The energy harvesting device of claim 1, wherein the insulated container is configured to be positioned within an item of athletic apparel.

* * * * *